United States Patent [19]

Horii et al.

[11] Patent Number: 4,945,046

[45] Date of Patent: Jul. 31, 1990

[54] YEAST PROMOTER AND PROCESS FOR PREPARING HETEROLOGOUS PROTEIN

[75] Inventors: Hajime Horii; Haruhide Kawabe; Hirofumi Arimura; Hiromichi Mukai; Kaoru Kobayashi; Muneo Tsujikawa, all of Osaka; Masayuki Nishida; Tadakazu Suyama, both of Kyoto, all of Japan

[73] Assignee: The Green Cross Corporation, Osaka, Japan

[21] Appl. No.: 57,143

[22] Filed: Jun. 3, 1987

[30] Foreign Application Priority Data

Jun. 3, 1986 [JP] Japan .................................. 61-127153
Sep. 26, 1986 [JP] Japan .................................. 61-227441

[51] Int. Cl.$^5$ ..................... C12P 21/00; C12N 15/00; C12N 5/00
[52] U.S. Cl. .................................. 435/69.3; 435/69.1; 435/172.3; 435/320; 435/255; 435/256; 935/37; 935/28; 935/69; 536/27
[58] Field of Search ................. 435/68, 70, 172.3, 320, 435/255, 256, 317.1; 935/32, 28, 37, 36, 69, 60, 65; 536/27

[56] References Cited

FOREIGN PATENT DOCUMENTS 0013828 12/1979 European Pat. Off. .............. 435/68
0164556 12/1985 European Pat. Off. .............. 435/68
0165759 12/1985 Japan ................................... 435/68

OTHER PUBLICATIONS

Bitter et al., Gene vol. 32, 1984, pp. 263–274 "Expression of Heterologous Genes in *Saccharomyces cerevisiae* from Vectors Utilizing the Glyceraldehyde-3-Phosphate Dehydrogenase Gene Promoter".
Khoury et al., Cell, vol. 33, pp. 313–314, Jun. 1983, "Enhancer Elements".
Valenzuela et al., Biotechnology, vol. 3, p. 317, 1985.

Errede et al., *Proc Natl Acad Sci*, vol. 82, pp. 5423–5427, 1985.
Jones et al., *Chem. Abst.*, vol. 104 (7), No. 49438g, 1988.
Gelfane et al., *Chem. Abst.*, vol. 104(25), No. 220131z, 1985 "Mammalian Promoters Useful in Yeast Expression".
Guarente et al., *Proc Natl Acad. Sci.*, vol. 79, Dec. 1982, pp. 7410–7414, "A Gal10–Cyc1 Hybrid Yeast Promotor Identifies the Gal4 Regulatory Region".
Murray et al., *EMBC*, vol. 3(3), pp. 645–650, 1984, "Hepatitis B Virus Antigens Made in Microbial cells Immunis Against Viral Infection".
Valenzuela et al., "Synthesis and Assembly in Yeast . . . Receptor", 6062 Biotechnology, 3 (1985) Apr., No. 4, London, Great Britain, pp. 317–320.
K. Struhl, "Genetic Properties and Chromatin . . . Sequence", Proc. Natl. Acad. Sci. U.S.A., vol. 81, pp. 7865–7869, Dec. 1984.

*Primary Examiner*—Robin Teskin
*Attorney, Agent, or Firm*—Sughrue, Mion, Zinn, Macpeak & Seas

[57] ABSTRACT

A method of producing a heterologous protein in yeast is disclosed, which comprises transforming a yeast *Saccharomyces cerevisiae* with recombinant DNA comprising a promoter selected from the group consisting of a yeast promoter or a hybrid promoter derived from a yeast promoter, particularly a hybrid promoter containing the enhancer region of SV40 virus, and a gene coding for a heterologous protein such as HBsAg and Pre S-HBsAg, particularly full length Pre S-HBsAg culturing, the resulting transformed cells to express the gene coding the heterologous protein, and isolating the heterologous protein from the cultured medium. GAP-DH and PH05 promoters and miniaturized ones can be used as the yeast promoter. The expression of the full length Pre S-HBsAg is carried out in the same expression system as that for 2nd or 3rd Pre S-ABsAg.

12 Claims, 17 Drawing Sheets

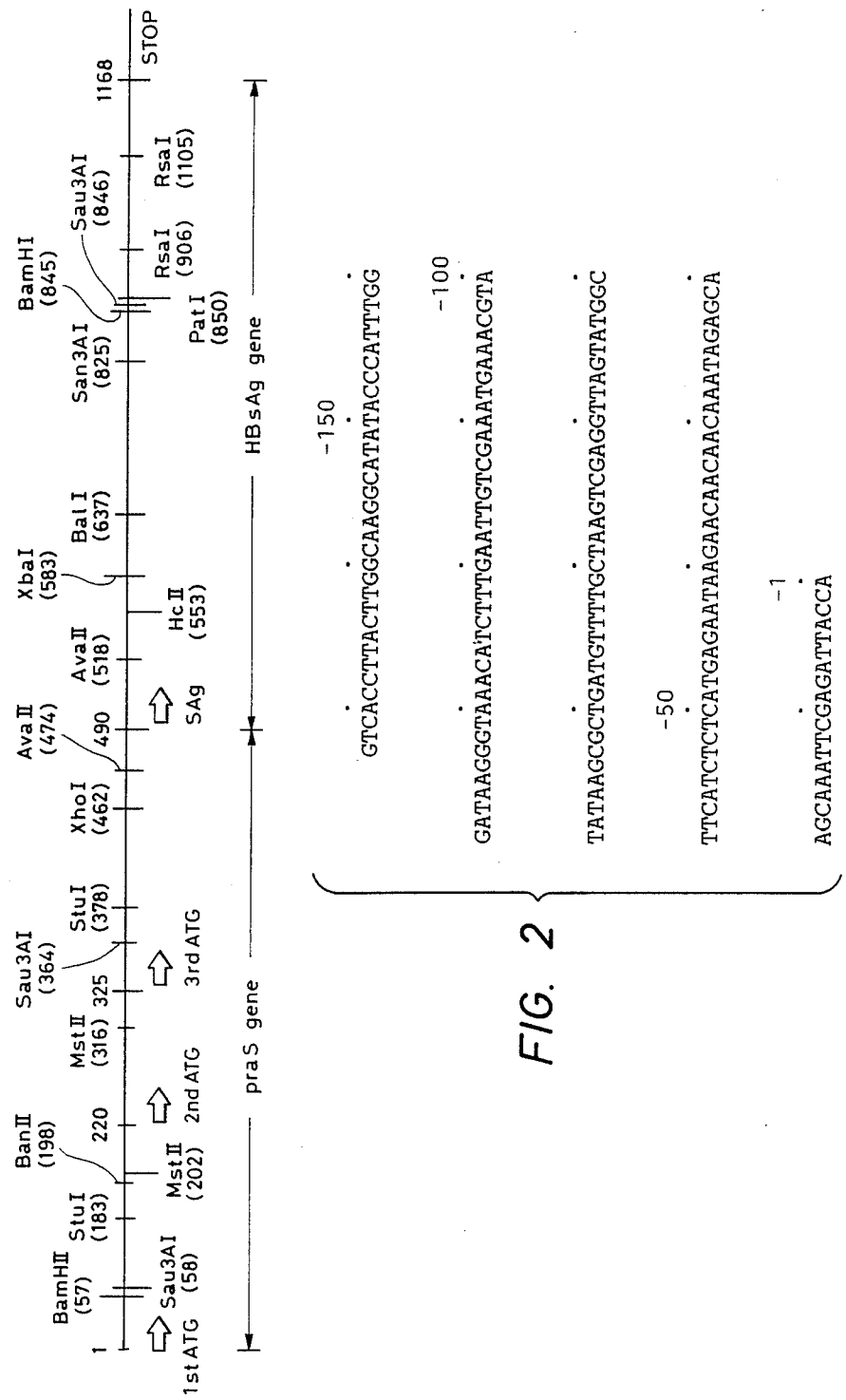

```
        -150                                                    -101
         .                        .                        .     .
TATTCCCCTACTGACTAATAAGTATATAAAGACGGTAGGTATTGATTGTAATTCTGTAAATCT
-100                      -50
 .                        .                        .
ATTTCTTAAACTTCTTAAATTCTACTTTTATAGTTAGTCTTTTTTTAGTTTTAAAACACCAAGAACTTAGTTTCG
```

YEAST PROMOTER AND PROCESS FOR PREPARING HETEROLOGOUS PROTEIN

FIELD OF THE INVENTION

The present invention relates to a method of producing heterologous proteins such as HBsAg and Pre S-HBsAg in yeast. Also, it relates to improved yeast promoters.

BACKGROUND OF THE INVENTION

Various attempts for producing heterologous proteins in yeast using genetic engineering technology have been made. For example, HB vaccine for preventing Hepatitis B, which has been prepared by collecting and purifying the surface antigen protein of HB virus (HBV) from HBsAg positive human plasma and thus suffered shortage of supply and high cost, is recently produced by genetic engineering technology. More particularly, HBV genome DNA is cloned and gene coding for the surface antigen is isolated therefrom and the resulting HBsAg gene is expressed in yeast (K. Murray et al., EMBO J., 3:3,645 (1984), G. A. Bitter & K. M. Egan, Gene, 32:263 (1984)) or in animal cells (M. F. Dubois et al., Proc. Natl. Acad. Sci., 77, 4549 (1980)) to give HB vaccine in large amounts.

The human serum-derived HBsAg is in the form of 22 nm particles which are mainly composed of the peptide P24 (molecular weight 24,000) and the peptide P27 (molecular weight 27,000), which is glycosylated form of P24. In addition, they contain a minute amount of human serum-derived HBsAg particles peptide P31 (molecular weight 31,000), which is composed of P24 and 55 amino acid residues attached to the N-terminus of P24 (hereinafter referred to "3rd Pre S-HBsAg"), and the peptide P33 (molecular weight 33,000), which is glycosylated form of P31. Further, HBV contains as the surface antigen the peptide P41, which is composed of P31 and 108 or 119 amino acid residues attached to the N-terminus of P31 (hereinafter referred to "1st Pre S-HBsAg"), and the peptide P43, which is glycosylated form of P41.

The amino acid sequence of P31 contains attached thereto 55 amino acid residues encoded by the Pre S region present upstream from S antigen gene. The region composed of 55 amino acid residues is found to be capable of binding polymerized human serum albumin (pHSA) (Machida et al., Gastroenterol., 85:268 (1983)). HBV is believed to invade and infect human hepatocytes through pHSA. From this it follows that the antibody to the polyalbumin receptor is expected to play an important role in the prevention of infection of HBV. Since the polyalbumin receptor is encoded by the Pre S region of HB virus, HBsAg having the Pre S region gene product, i.e., Pre S-HBsAg, is believed to induce increased antibody production in humans as compared with HBsAg having no Pre S region polypeptide.

Peptide P31 composed of S antigen containing 55 amino acid sequence encoded by the Pre S region of HBV, i.e., 3rd Pre S-HBsAg, has been produced in large amounts by gene engineering technology using as a host yeast (P. Valenzuela et al., BIO/TECHNOLOGY, 3:317 (1985)) or animal cell (M. L. Michel et al., Proc. Natl. Sci., 81:7708 (1984)).

When the expression of genes coding for HBsAg by gene engineering technology is carried out HBsAg, 3rd Pre S-HBsAg and amino acid sequence composed of 3rd Pre S-HBsAg (2nd Pre S-HBsAg) and additional 35 amino acid residues attached to the N-terminus thereof can form particles in large amounts independently of others in contrast to 1st Pre S-HBsAg which is difficult to produce in large amounts by the expression of the gene coding therefor in yeast or animal cell independently of others.

On the other hand, when heterologous proteins are produced in yeast by gene engineering technology promoter regions of yeast origin, e.g., PH05 (K. Murray et al., EMBO J., 3 (3):645–650 (1984)), GAP-DH (G. A. Bitter & K. M. Eagan, Gene, 32:263–274 (1984)), PGK (C. Y. Chen et al., Nucl. Acid Res., 12 (23):8951–8970 (1984)), and α-Factor (A. J. Brake et al., Proc. Natl. Acad. Sci., U.S.A., 81:4642–4646 (1984)) are used. Generally, the promoter region in yeast in which RNA polymerase II acts is composed of two regions one containing the portion starting from the translation initiation site through the transcription initiation site and TATA box and another containing upstream activation site (UAS) which is present on the 5' side of the above-described region and functions in the cis mode to promote the transcription. (C. Guarente, Cell: 36, 799 (1984)). It has been shown that the UAS promotes the transcription of specific gene upon the action of a factor functioning in the trans mode in the cell (E. Giniger et al., Cell, 40:767–774 (1985)). Also, it has been shown that since the UAS functions independently of the region containing the sequence starting from the translation initiation site through the transcription initiation site the replacement of this UAS with the UAS of another gene leads to the release of the promoter from the original control system and the placement of the promoter under the control involving the new substitute UAS (L. Guarente et al., Proc. Natl. Acad. Sci., U.S.A., 79:7410 (1982); L. Guarente et al., Cell, 36:503 (1984); K. Struhl, Proc. Natl. Acad. Sci., U.S.A., 81:7865 (1984)).

The existence of enhancers which function in the cis mode to promote the transcription in the transcription-controlling region in the genes of animal cells and animal virus such as SV40 virus is shown (G. Khoury & P Gruss, Cell, 33:313–314 (1983)). Further, it has been shown that the enhancer of SV40 virus can function in the kidney cells of Green monkey (D. H. Hamer & P. Leder, Nature, 281:35 (1979)), COS cells (Humphries et al., Cell, 30:173 (1982)) and Hela cells (J. Banerji et al., Cell, 27:299 (1981)). Whether the enhancer of SV40 virus can function in yeast or not is unknown. However, it is interesting that it is shown that the Ty element of yeast contains a sequence homologous to the sequence of SV40 enhancer (B. Errede et al., Proc. Natl. Acad. Sci., U.S.A., 82:5423–5427 (1985)).

SUMMARY OF THE INVENTION

An object of the present invention is to produce heterologous proteins in yeast.

Another object of the present invention is to produce the full length Pre S region-containing HBsAg in yeast.

Still another object of the present invention is to provide a hybrid promoter comprising a yeast promoter having incorporated therein an SV40 virus-derived enhancer.

Yet another object of the present invention is to produce heterologous proteins such as HBsAg and Pre S-HBsAg in yeast using a hybrid promoter comprising a yeast promoter having incorporated therein an SV40 virus-derived enhancer.

As a result of extensive investigation it has now been found that simultaneous expression of HBsAg, 3rd Pre S-HBsAg or 2nd Pre S-HBsAg together with 1st Pre S-HBsAg in the same cell has led to the successful production of 1st Pre S-HBsAg as well as other HBsAg proteins.

Further, it has been found that replacement of the UAS with an SV40 virus enhancer releases the promoter from its normal control system and the promoter comes under the control of the enhancer giving rise to improved promotional activity.

The present invention is based on the above discoveries and provides a method of producing a heterologous proteins in yeast, which comprises transforming a yeast *Saccharomyces cerevisiae* with recombinant DNA comprising a promoter selected from the group consisting of a yeast promoter or a hybrid promoter derived from a yeast promoter, particularly a hybrid promoter containing the enhancer region of SV40 virus, and a gene coding for a heterologous protein such as HBsAg and Pre S-HBsAg, particularly full length Pre S-HBsAg, culturing the resulting transformed cells to express the gene coding the heterologous protein, and isolating the heterologous protein from the cultured medium.

In another aspect, the present invention provides a hybrid promoter comprising a yeast promoter from which the upstream activation site is deleted, and an enhancer derived from SV40 virus.

BRIEF DESCRIPTION OF THE DRAWINGS

FIG. 1 shows the restriction map of the Pre S-HBsAg gene used in the present invention;

FIG. 2 shows the base sequence of a miniaturized PHO5 promoter;

In the figures:

Figures 3, 4:
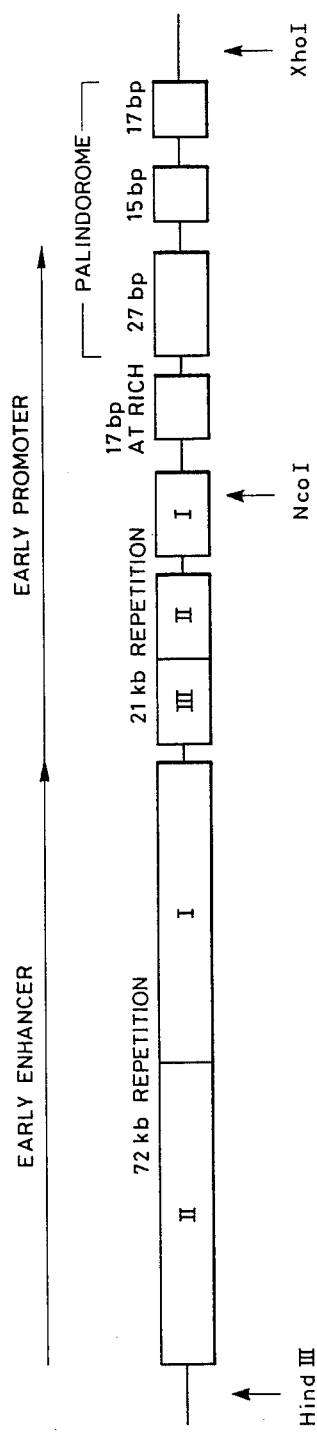
FIG. 3 shows the base sequence of a miniaturized GAP-DH promoter.
FIG. 4 shows the transcription regulatory region of SV40 and the restriction enzyme recognition sites thereon.

| | |
|---|---|
| 1 = | ... GAP-DH gene, |
| 2 = | ... GAP-DH promoter, |
| 3 | GAP-DH promoter DNA fragment, |
| 4 = | ... Terminator for GAP-DH gene, |
| 5 | DNA fragment containing 4, |
| 6 | 1.3 kb DNA fragment containing HBsAg gene, |
| 7 = | ... HBsAg gene, and |
| 8 = | ... Pre S gene. |

DETAILED DESCRIPTION OF THE INVENTION

The DNA sequence of Pre S is known and plasmids carrying Pre S are also known (*Molecular Cloning*, Cold Spring Harbor Laboratory (1982) and J. D. Beggs, *Nature*, 275: 104 (1978)). For example, the sequence shown in Table 1 is known as the full length DNA sequence of Pre S. In the examples of present invention, the plasmid pPre S (FIG. 1) commercially available from Biogen was employed.

TABLE 1

DNA and Amino Acid Sequence of Pre S

| 1 | | | | | | | | |
|---|---|---|---|---|---|---|---|---|
| Met | Gly | Gln | Asn | Leu | Ser | Thr | Ser | Asn |
| ATG | GGG | CAG | AAT | CTT | TCC | ACC | AGC | AAT |
| 10 | | | | | | | | |
| Pro | Leu | Gly | Phe | Phe | Pro | Asp | His | Gln | Leu |
| CCT | CTG | GGA | TTC | TTT | CCC | GAC | CAC | CAG | TTG |
| 20 | | | | | | | | |
| Asp | Pro | Ala | Phe | Arg | Ala | Asn | Thr | Asn | Asn |
| GAT | CCA | GCC | TTC | AGA | GCA | AAC | ACC | AAC | AAT |
| 30 | | | | | | | | |
| Pro | Asp | Trp | Asp | Phe | Asn | Pro | Asn | Lys | Asp |
| CCA | GAT | TGG | GAC | TTC | AAT | CCC | AAC | AAG | GAC |
| 40 | | | | | | | | |
| Thr | Trp | Pro | Asp | Ala | Asn | Lys | Val | Gly | Ala |
| ACC | TGG | CCA | GAC | GCC | AAC | AAG | GTA | GGA | ACT |
| 50 | | | | | | | | |
| Gly | Ala | Phe | Gly | Leu | Gly | Phe | Thr | Pro | Pro |
| GGA | GCA | TTC | GGG | CTA | GGG | TTC | ACC | CCA | CCG |

TABLE 1-continued

DNA and Amino Acid Sequence of Pre S

| | 60 | | | | | | | | |
|---|---|---|---|---|---|---|---|---|---|
| His | Gly | Cly | Leu | Leu | Gly | Trp | Ser | Pro | Gln |
| CAC | GGA | GGC | CTT | TTG | GGG | TGG | AGC | CCT | CAG |
| | 70 | | | | | | | | |
| Aka | Gln | Gly | Ile | Met | Gln | Thr | Leu | Pro | Ala |
| GCT | CAG | GGC | ATA | ATG | CAA | ACC | TTG | CCA | GCA |
| | 80 | | | | | | | | |
| Asn | Pro | Pro | Pro | Ala | Ser | Thr | Asn | Arg | Gln |
| ATT | CCG | CCT | CCT | GCC | TCT | ACC | AAT | CGC | CAG |
| | 90 | | | | | | | | |
| Ser | Gly | Arg | Arg | Pro | Thr | Pro | Leu | Ser | Pro |
| TCA | GGA | CGG | CAG | CCT | ACC | CCG | CTG | TCT | CCA |
| 100 | | | | | | | | | |
| Pro | Leu | Arg | Thr | Thr | His | Pro | Gln | Ala | |
| CCT | CTG | AGA | ACC | ACT | CAT | CCT | CAG | GCC | |
| | | 110 | | | | | | | |
| Met | His | Trp | Asn | Ser | Thr | Thr | Phe | His | Gln |
| ATG | CAC | TGG | AAC | TCC | ACA | ACC | TTC | CAC | CAA |
| 3rd | | | | | | | | | |
| | | 120 | | | | | | | |
| Thr | Leu | Gln | Asp | Pro | Arg | Val | Arg | Gly | Leu |
| ACT | CTG | CAA | GAT | CCC | AGA | GTR | AGA | GGC | CIG |
| | | 130 | | | | | | | |
| Tyr | Phe | Pro | Ala | Gly | Gly | Ser | Ser | Ser | Gly |
| TAT | TCC | CCT | GCT | GGT | GGC | TCC | AGT | TCA | GGG |
| | | 140 | | | | | | | |
| Thr | Val | Asn | Pro | Val | Pro | Thr | Thr | Thr | Ser |
| ACA | GTA | AAC | CCT | GTT | CCG | ACT | ACT | ACC | TCT |
| | | 150 | | | | | | | |
| Pro | Ile | Ser | Ser | Ile | Phe | Ser | Arg | Ile | Gly |
| CCC | ATA | TCG | TAC | ATC | TTC | TCG | AGG | ATT | GGG |
| | | 160 | | | | | | | |
| Asp | Pro | Ala | Leu | Asn | | | | | |
| GAC | CCT | GCG | CTG | AAC | | | | | |

The Pre S-HBsAg gene has the restriction enzyme map shown in FIG. 2. The DNA sequence of the HBsAg gene is also known and plasmids carrying said gene are known.

While HBsAg includes the subtypes adw (Valenzuela et al, Nature, 280:815–819 (1979), ayw (Charnay et al, Proc. Natl. Acad. Sci., U.S.A., 76:2222–2226 (1979), ad/yw Pasek et al, Nature, 282:575–579 (1979), etc., HBsAg subtype ad/yw was employed in the example of the present invention.

The expression vector to be used in the practice of the present invention is a vector containing an Escherichia coli gene and a yeast gene and further a yeast promoter.

Suitable example of the yeast promoter which can be used in the present invention include the miniaturized PHO5 promoter and miniaturized GAP-DH promoter.

The PHO5 promoter is the promoter region of a yeast gene coding for repressible acid phosphatase (PHO5). It is known that the activity of this promoter is repressed when the medium contains inorganic phosphoric acid and increased when the medium is deficient in inorganic phosphate. Therefore, it is necessary to use a medium which contains no inorganic phosphoric acid or a mutant yeast strain in which the DNA sequence coding for the PHO5 control system contains mutated portion and the PHO5 promoter functions constitutively.

The deletion of the UAS region from the PHO5 promoter is carried out upstream (5' side) of the Bst EII recognition site in the vicinity of −70 bp from TATA box. FIG. 3 shows the nucleotide sequence of the miniaturized PHO5 promoter.

The GAP-DH promoter is the promoter region of a yeast gene coding for glyceraldehyde-3-phosphate dehydrogenase (GAP-DH) which constitutes yeast glycolytic pathway and this promoter functions constitutively within the yeast cell. The deletion of the UAS region from the GAP-DH promoter is carried out upstream (5' side) of the Xmn I-recognizable site in the vicinity of −20 bp from TATA box. FIG. 4 shows the nucleotide sequence of the miniaturized GAP-DH promoter.

Preferably, the vector used in the present invention carries a hybrid promoter obtained by replacing the UAS region of a yeast promoter with the SV40 virus enhancer.

The DNA sequence of the transcription regulatory region of SV40 virus is known and plasmids carrying it is also known and commercially available from Pharmacia AB, etc. A region including 72 bp repeat structure or early enhancer, which can be obtained from plasmids carrying the transcription regulatory region using a known restriction enzyme. FIG. 4 schematically illustrates the transcription regulatory region of SV40 and the restriction enzyme recognition sites thereof.

The yeast strain to be transformed is suitably a mutant with a mutation complementary to the selection marker gene borne by the plasmid to be inserted, for example, the leucine-requiring mutant Saccharomyces cerevisiae AH22 (a, his4, leu2, can1) deposited at American Type Culture Collection, 12301 Parklawn Drive, Rockville, Md. 20852-1776 under ATCC No. 38626 (G. Fink, Proc. Natl. Acad. Sci., U.S.A., 75, 1929 (1978)). The transformed yeast obtained is cultivated on a known medium suited for the host, for example, YNB liquid medium comprising 0.7% (w/v) Yeast Nitrogen Base (Difco), 2% (w/v) glucose and YPD liquid medium comprising 1% yeast extract (Difco), 2% polypeptone (Daigo Eiyo Kagaku) and 2% (w/v) glucose. The cultivation is carried out generally at 15° to 32° C. for 20 to 50 hours, with aeration and/or stirring, if desired. After cultivation, the cells are collected by a known method, for example, by centrifugation and then disrupted, for example, by suspending them in an appropriate buffer solution and subjecting the suspension to sonication. Thereafter, the supernatant is recovered. This supernatant contains the desired product HBsAg or Pre S-HBsAg and this desired substance is purified, for example, by affinity chromatography using a column with a monoclonal antibody or polyalbumin immobilized thereon or by affinity chromatography based on hydrophobic groups.

A large number of techniques, reaction methods and analytical methods are well known in the art relative to the practice of the invention. Unless otherwise specified, all of the enzymes are commercially available, for example, from Takara Shuzo, Japan; New England Biolabs (NEB), Mass., U.S.A.; Amersham, Great Britain; and Bethesda Research Laboratories (BRL), Md., U.S.A.

Unless otherwise specified, the buffer and reaction conditions for each enzymatic reaction were as recommended by the manufacturer of the enzyme used.

Transformation of *Escherichia coli* utilizing a phage, transformation of *Escherichia coli* with a plasmid, plaque hybridization, electrophoresis and recovery of DNA from the gel were carried out as described in *Molecular Cloning*, supra. Yeast transformation was conducted as described in *Methods in Yeast Genetics*, Cold Spring Harbor Laboratory (1981).

Suitable examples of *Escherichia coli* strains which can be used in the present invention include *E. coli* HB101 available from Takara Shuzo (D. Hanahan, *J. Mol. Biol.*, 166, 557 (1983)), *E. coli* JM109 available from Takara Shuzo (J. Messing, *Gene*, 33, 103 (1985)), *E. coli* RRI available from BRL (Md., U.S.A.) (D. Hanahan, *J. Mol. Biol.*, 166, 557 (1983)), and those disclosed in *Molecular Cloning*, supra.

The 1st Pre S-HBsAg produced according to the present invention when used as vaccine stimulates the production of an anti-albumin receptor antibody as well as an anti-HBsAg antibody.

In the blood of patients with hepatitis B or HB vaccine recipients there is found an antibody to a peptide on the N-side of the 1st Pre S region. The occurrence of this antibody well coincides with that of each virus marker of hepatitis B (Neurath et al., *Vaccines*, 86:371-375, Cold Spring Harbor Laboratory). The antibody is expected to give some contribution to the prevention of the infection of HBV. It is also expected that the production of the antibody is stimulated by the 1st Pre S-HBsAg.

The production system comprising yeast carrying the hybrid promoter comprising the SV40 enhancer region and the miniaturized yeast promoter enables efficient expression of a gene coding for heterologous protein connected at its downstream end in a manner suitable for expression and increases the yield of the product as compared with the case where original yeast promoter is used. Hybrid promoters comprising as the miniaturized yeast promoter the PHO5 promoter, which originally functions repressibly, functions constitutively in yeast cells since the region having a PHO5 transcription-promoting activity is deleted. Further, since the region derived from yeast in the promoter is reduced to ⅓ to 1/5 time the original size the frequency of recombination with the chromosome of host yeast will be decreased and thus the expression of heterologous genes will be stabilized.

The following reference examples and working examples illustrate the invention in more detail but are by no means limitative of the invention.

REFERENCE EXAMPLE 1

Cloning of the yeast PHO5 gene and PHO5 promoter

DNA having the yeast PHO5 gene was prepared from yeast chromosomal DNA in the following manner.

The chromosomal DNA was extracted from *Saccharomyces cerevisiae* GRF (α, trp, his, met) obtained from Biogen S.A. (Erhart, E. & Hollenberg, C.P., *J. Bacteriol.*, 156:625 (1983)) by the method of C. R. Cryer et al, *Methods in Cell Biology*, Vol. XII, Chapter 3, page 39, Accademic Press, New York (1975).

Then, cloning of the PHO5 gene was carried out according to the report of B. Meyback et al., *EMBO J.*, 1:675 (1982). More specifically, the chromosomal DNA thus obtained was digested with the restriction enzyme Bam HI (Takara Shuzo; the same shall apply hereinafter). The about 5.1 kb DNA fragment was recovered by subjecting the Bam HI-digested DNA to electrophoresis using 0.8% agarose gel. This DNA fragment was joined to the pUC9 (Takara Shuzo, J. Messing, Methods in Enzymology, 101:20 (1983)) DNA at the Bam HI site in the poly linker sequence using T4 DNA ligase. The ligation product was used to transform the *Escherichia coli* strain HB101 (F−, hsdS20($r_B^-$, $m_B^-$), recA13, ara-14, proA2, lacY1, galK2, rpsL20(SM$^r$), xyl-5, mtl-1, supE44, λ−) (Takara Shuzo) and cloning was performed. The transformation of the *Escherichia coli* strain with the plasmid was performed as described in *Molecular Cloning*, supra. The transformed cells were subjected to colony hybridization using a synthetic polynucleotide as a probe according to the method described in *Molecular Cloning*, supra. Plasmids (pUCPho) were prepared from the positive colony and digested with Bam HI to recover the inserted DNA fragment, which then was joined to the Bam HI site of the plasmid pJDB207. The plasmid thus obtained was recloned. The recloned plasmid was used to transform *Saccharomyces cerevisiae* AH22 (a, his4, leu2, can1). The PHO5 activity (repressible acid phosphatase activity) of the transformed cells was confirmed by the method of Toh-e, A. et al., *J. Bacteriol.*, 113:727 (1973). The repressible acid phosphatase-positive plasmid, pUCPho, was digested with Bam HI-HPa I and the 3.9 kb DNA fragment was recovered by subjecting the DNA after digestion with Bam HI-HPa I to electrophoresis 1% agarose. The DNA fragment was inserted at the Bam HI-Eco RV site of the plasmid pBR322 to obtain the plasmid pAP5 (8 kb).

REFERENCE EXAMPLE 2

Figure 5A:
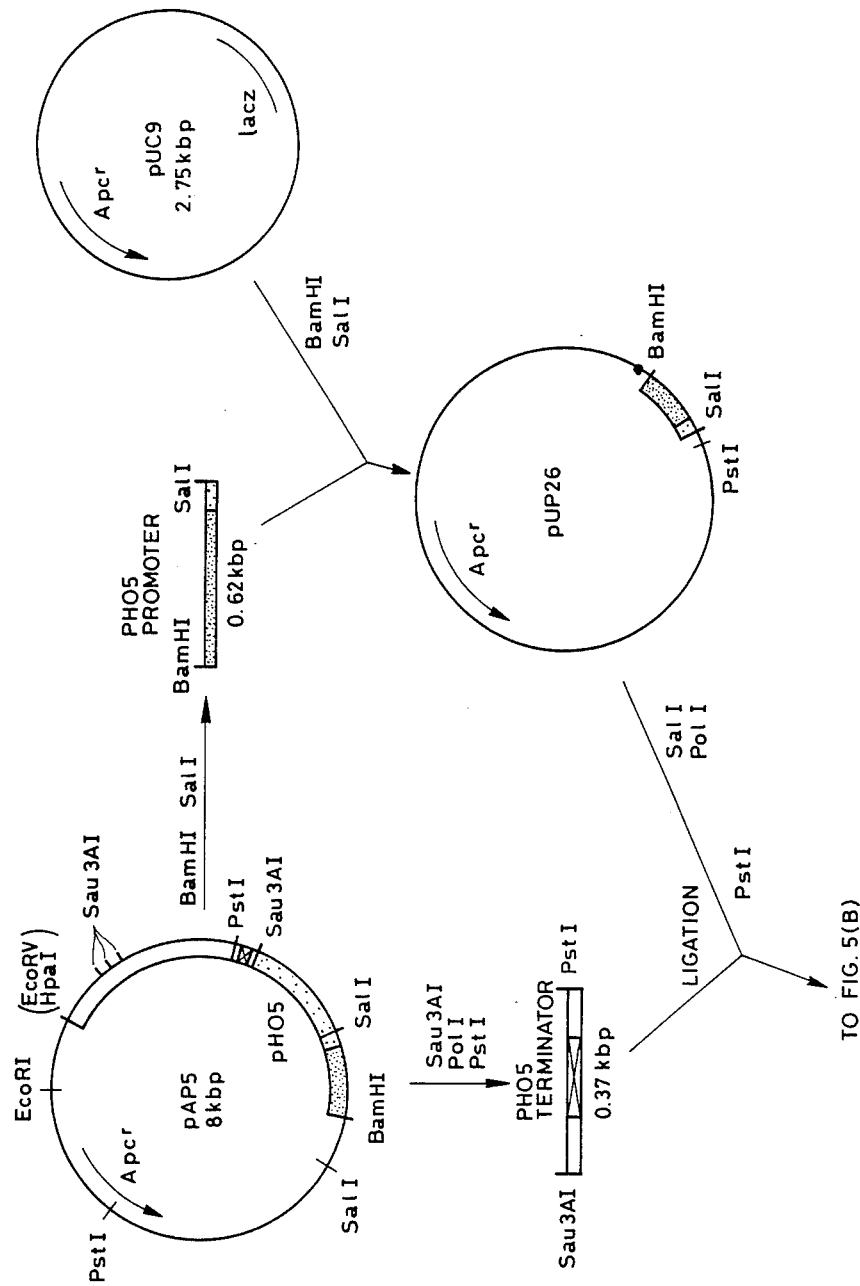
FIG. 5(A) and FIG. 5(B) show a scheme for preparing the HBsAg production plasmid pGL2062 (Reference Example 2)
Figure 5B:
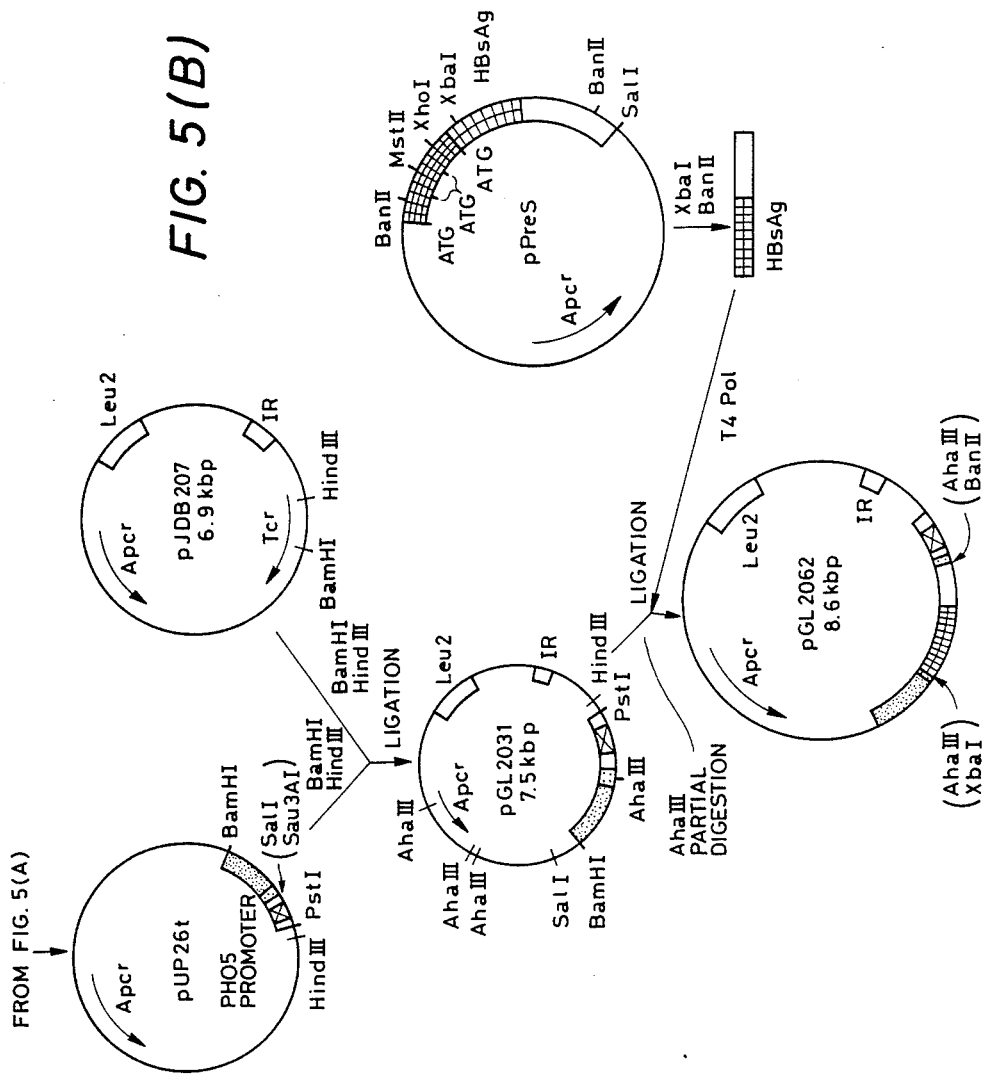

Preparation of the HBsAg expression plasmid using the PHO5 promoter (FIG. 5).

PHO5 promoter fragment containing the ATG codon of PHO5 (0.62 kb) was prepared by digesting pAP5 with Bam HI-Sal I and subjecting the digested DNA fragments to electrophoresis using 4% polyacrylamide gel (PAGE). The 0.62 kb DNA fragment was inserted at the Bam HI-Sal I site in the base sequence of the pUC polylinker to obtain the plasmid pUP26.

A PHO5 terminator fragment (0.37 kb) was prepared by digesting pAP5 with Sau 3AI, rendering blunt-ended with DNA polymerase I (Klenow fragment) (Boehringer-Mannheim), further digesting the thus-treated DNA fragment and subjecting the resulting DNA fragments to electrophoresis using 4% PAGE. On the other hand, pUP26 was digested with Sal I and the ends of the resulting DNA fragment was blunt-ended with CNA polymerase I (Klenow fragment) followed by digestion with Pst I. The above-described PHO5 terminator was ligated to the Pst I-digested DNA fragment to obtain the plasmid pUP26t. A 0.99 kb DNA fragment containing the PHO5 promoter-terminator was recovered by digesting pUP26t with Bam HI-Hind III and subjecting the resulting DNA fragments to electrophoresis using 4% polyacrylamide gel. The 0.99 kb fragment was inserted at the Bam HI-Hind III site of pJDB207 to obtain a plasmid pGL2031.

The plasmid pPre S carrying the Pre S-HBsAg gene (Biogen) was completely digested with the restriction enzymes Xba I (Takara Shuzo) and Bam II (NEB) followed by electrophoresis using 1.5% agarose gel to prepare a 1.1 kb DNA fragment containing the HBsAg gene. On the other hand, pGL2031 was partially digested with the restriction enzyme Aha III (Takara Shuzo) followed by electrophoresis using 0.8% agarose gel to recover pGL2031 with a single cut. The 1.1 kb HBsAg DNA fragment which had been treated with DNA polymerase I (Klenow fragment) to render the cohesive ends blunt was inserted to the pGL2031 thus recovered to prepare pGL2062.

REFERENCE EXAMPLE 3

Preparation of pGP3Hr

Figure 6:
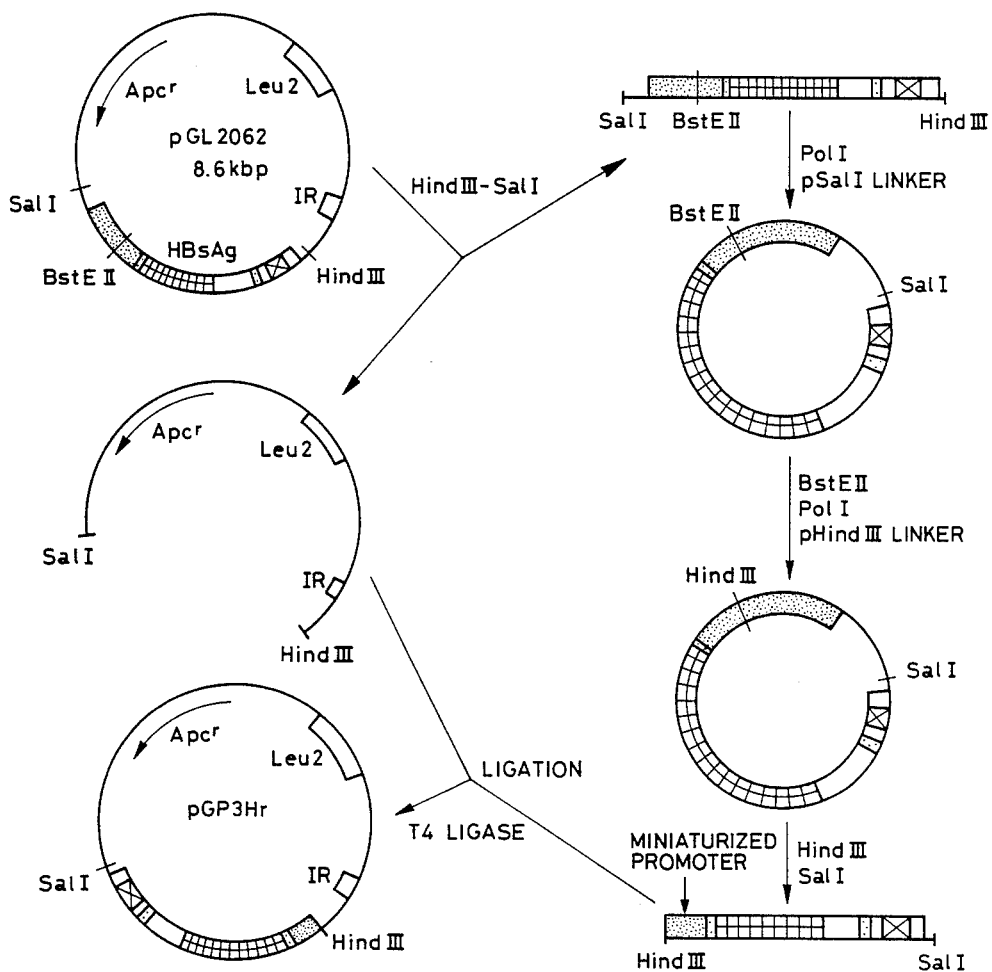
FIG. 6 shows a scheme for preparing the HBsAg production plasmid pGP3Hr which carries the miniaturized PHO5 promoter.

Plasmid pGP3Hr was prepared by the procedures illustrated in FIG. 6.

A 2.45 kb DNA fragment containing the PHO5 promoter, HBsAg and PHO5 terminator and a 6.3 kb DNA fragment which corresponds to the vector portion were obtained by completely digesting pGL2062 with the restriction enzyme Hind III (Takara Shuzo) and further digesting the product with the restriction enzyme Sal I (Takara Shuzo) followed by electrophoresis using 1% agarose gel. The cohesive ends of the 2.46 kb DNA fragment were rendered blunt in the presence of all of the four dNTPs using DNA polymerase I (Klenow fragment) (Boehringer-Mannheim) and the pSal I linker (Takara Shuzo) was ligated to the resulting DNA fragment using T4 DNA ligase (Takara Shuzo). The product was completely digested with the restriction enzyme Bst EII (NEB) followed by rendering the cohesive ends blunt-ended as described above. A pHind III linker (Takara Shuzo) was ligated to the product using T4 DNA ligase. The resulting DNA fragment was further digested completely with Hind III and Sal I followed by electrophoresis using 0.8% agarose gel. As a result, a 1.73 kb DNA fragment containing a miniaturized PHO5 promoter from which the base sequence upstream the Bst EII recognition site had been removed and which contains a Hind III-attachment site at the 5' side end of the PHO5 promoter and an Sal I-attachment site downstream from the 3' side end from the PHO5 terminator. The 1.73 kb DNA fragment and the 6.3 kb vector fragment were ligated with T4 DNA ligase to obtain pGP3Hr.

REFERENCE EXAMPLE 4

Cloning of the yeast GAP-DH gene

DNA having the yeast GAP-DH gene was prepared from yeast chromosomal DNA in the following manner.

The chromosomal DNA was prepared from Saccaromyces cerevisiae GRF18 (α, leu, trp, his, met) obtained from Biogen S.A. (Erhart, E. & Hollenberg, C.P., J. Bacteriol., 156:625 (1983)) by the method of C. R. Cryer et al, Methods in Cell Biology, Vol. 18, Chapter 3, page 39, Academic Press, New York (1975).

A 20-μg portion of this chromosomal DNA was completely digested with 10 units (U) of the restriction enzyme Hind III (Takara Shuzo; the same shall apply hereinafter) and joined with 1 μg of lambda phage charon 28 (B1007, KH54, N1N5) DNA also compoetely digested with 1 U of Hind III. For the joining reaction, T4 DNA ligase (Takara Shuzo; the same shall apply hereinafter) was used. The reaction was carried out overnight at 16° C. following the recommended procedure. The same method was also used in the DNA joining or ligation reactions to be mentioned hereinafter. The ligated product DNA was packaged using an in vitro packaging kit (Amersham) and then used to transfect the Escherichia coli strain LE392 (F-, hsdR514, ($r_k^-$, $m_k^-$), supE44, supF58, lacY1, galK2, galT22, metB1, trpR55, λ-) obtained from Stratagene (San Diego, U.S.A.) (Murray, N. E., Brammer, W. J. & Murray, K., Mol. Gen. Genet., 150:53 (1977)). In this manner, 40,000 plaques were obtained. The packaging was performed as recommended by Amersham and the transfection of Escherichia coli was conducted as described in Molecular Cloning, supra.

These 40,000 plaques were screened by immobilizing them on a nitrocellulose filter and then hybridizing them with $^{32}$P-labeled synthetic DNA (plaque hybridization). The synthetic DNA had the base sequence corresponding to 19th to 33rd from the first ATG of the GAP-DH gene (AACGGTTTCGGTAGA) reported by J. P. Holland et al (J. Biol. Chem., 254, 19, 9839 (1979)). The plaque hybridization was conducted as described in Molecular Cloning, supra. As a result, two phages capable of strong hybridization and agreeing in restriction enzyme mapping were obtained.

A yeast chromosome-derived 2.1 kb DNA fragment was prepared by completely digesting 10 μg of this phage DNA with 10 U of HindIII. The 2.1 kb DNA fragment was recovered by subjecting the completely HindIII-digested DNA to electrophoresis using low-melting agarose (BRL) in a concentration of generally 0.5 to 1.5%, preferably 0.7 to 1%, excising the 2.1 kb DNA fragment gel segment, extracting the DNA with phenol after 10-minute of heat treatment at 65° C. as recommended by BRL and precipitating the DNA from the aqueous layer with ethanol. The DNA fragment recoveries described hereinafter were always carried out by the above method.

A 1-μg portion of this 2.1 kb HindIII DNA fragment was joined to 1-μg of the pBR322 DNA, a typical Escherichia coli-derived plasmid, which had been completely digested with 1 U of HindIII using 5 U of T4 DNA ligase. The ligation product was used to transform the Escherichia coli strain HB101 (F-, hsdS20($r_B^-$, $m_B^-$), recA13, ara-14, proA2, lacY1, galK2, rpsL20(Sm$^r$), xyl-5, mtl-1, supE44, λ-) (Takara Shuzo) and cloning was performed. The transformation of the Escherichia coli strain with the plasmid was performed as described in Molecular Cloning, supra. The plasmid obtained by the above cloning was named pGAP301 (FIG. 7).

REFERENCE EXAMPLE 5

Construction of HBsAg expression vector

Figure 7A:
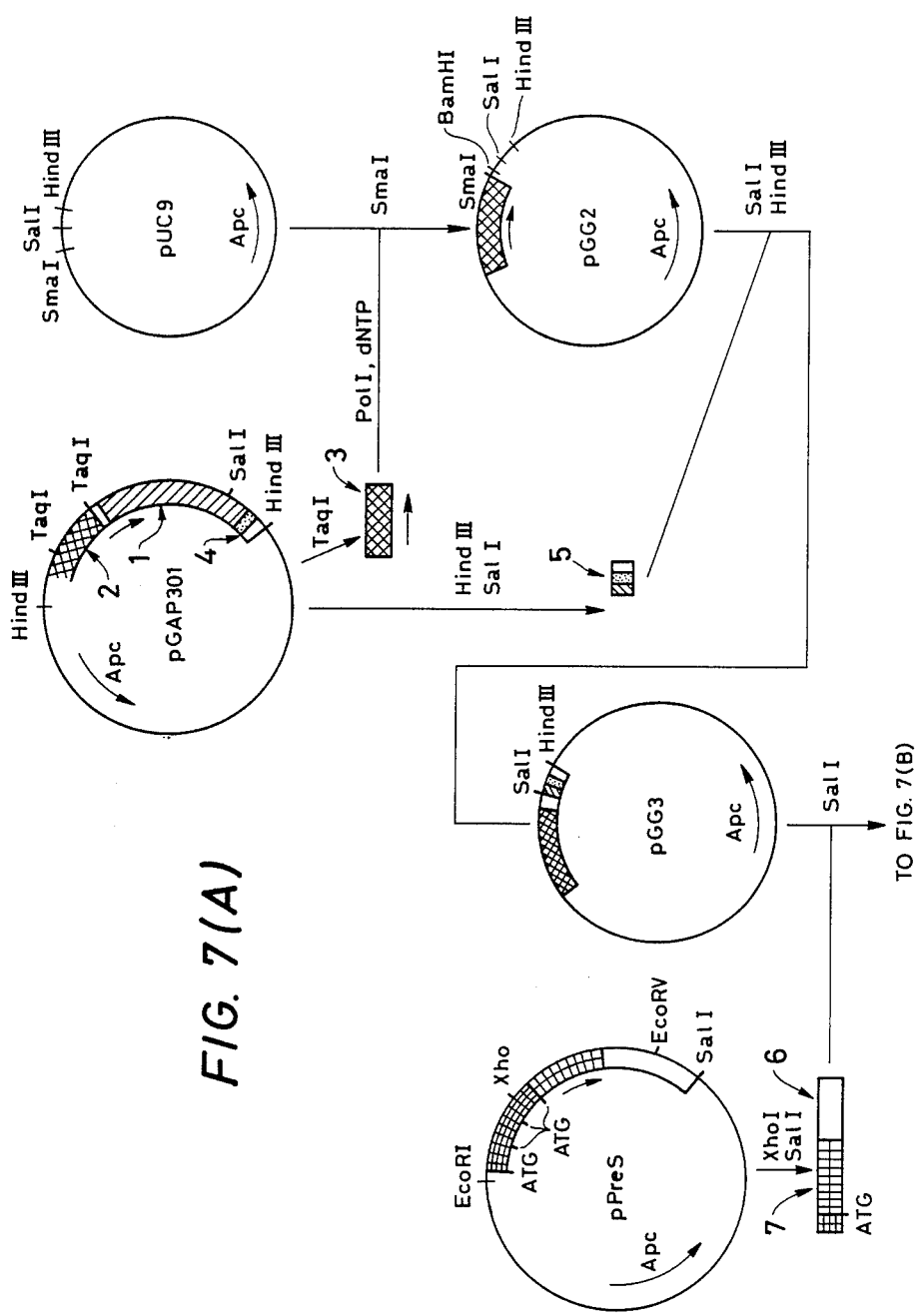
FIG. 7(A) and FIG. 7(B) show a scheme for preparing the HBsAg production plasmid pGG5 which carries the miniaturized GAP-DH promoter.
Figure 7B:
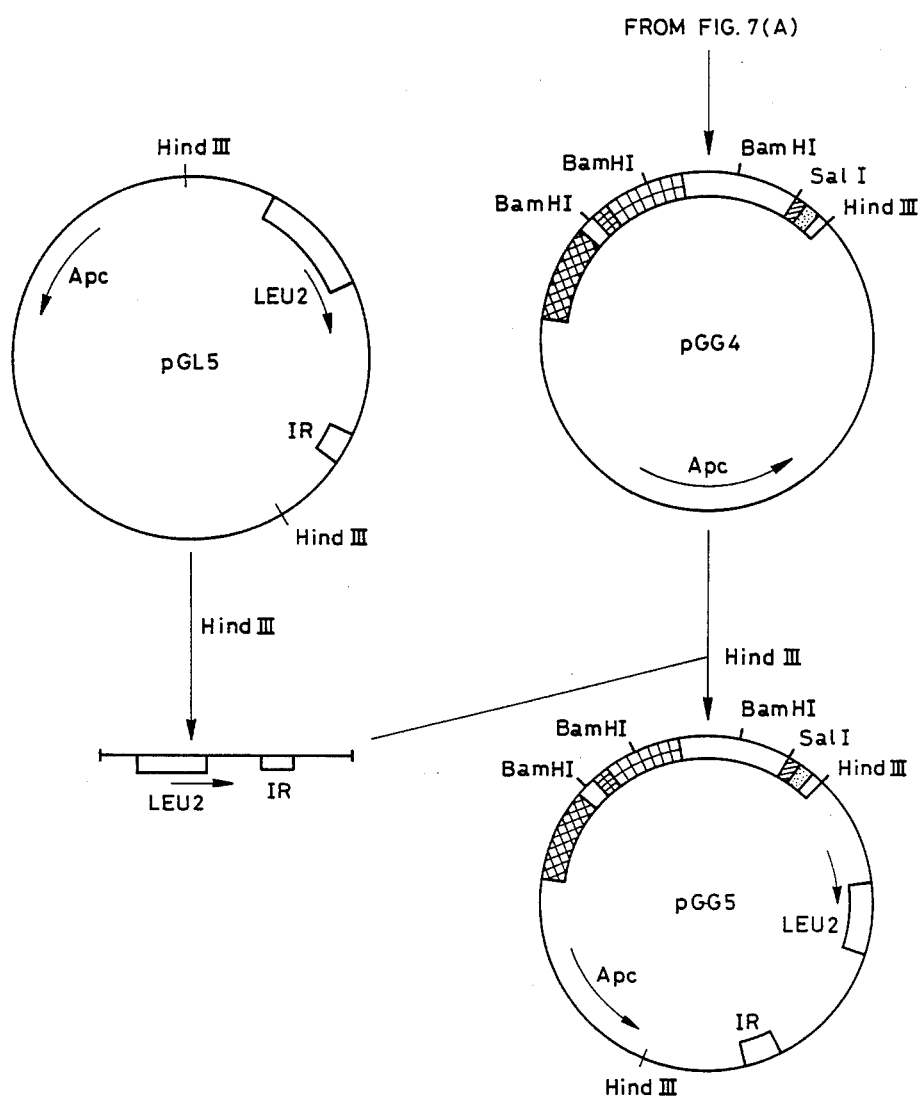
Figure 8:
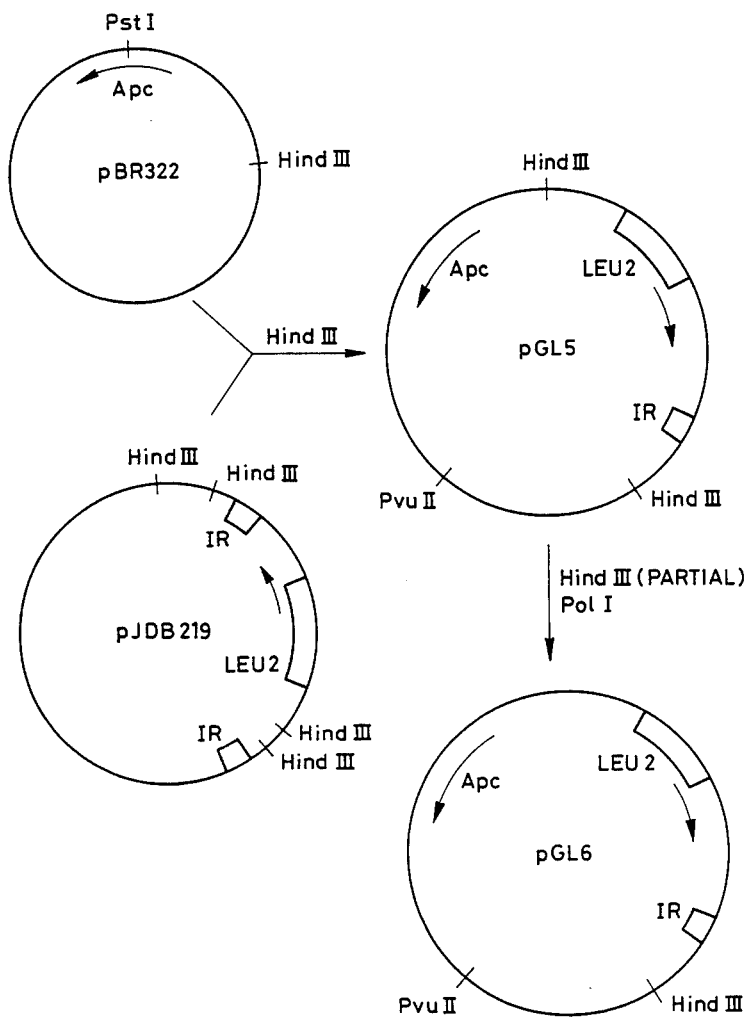
FIG. 8 shows a scheme for preparing the plasmids pGL5 and pGL6.

A plasmid vector, pGG5, using the GAP-DH promoter for the expression of HBsAg (hepatitis B virus surface antigen) in yeast was constructed as illustrated in FIG. 7 and FIG. 8. Referring to these figures, the construction of pGG5 is described below.

The DNA fragment 3 was prepared by complete digestion of 4 μg of the pGAP301 DNA with 1 U of TaqI (NEB) followed by electrophoretic isolation. This fragment was derived from the region of the GAP-DH promoter 2 and contained 652 bp from −676 to −25 with the base of the translation initiation site of the GAP-DH gene 1 being taken as +1.

The cohesive ends of this DNA fragment 3 was rendered blunt by treatment with 1 U of DNA polymerase I (Pol I) (Takara Shuzo) and 0.1 μg dNTP (deoxyNTP). pUC9 [Takara Shuzo (J. Messing, Methods in *Enzymology*, 101, 20 (1983))] (1 μg) was completely digested with 1 U of SmaI (Takara Shuzo) and ligated with the above blunt-ended DNA fragment in the direction shown in FIG. 7(A) using 5 U of T4 DNA ligase. The resulting DNA was used to transform *Escherichia coli* HB101 and the thus-obtained plasmid was named pGG2.

Then, the 140 bp DNA fragment 5 containing the terminator sequence 4 of the GAP-DH gene was prepared by completely digesting 10 g of pGAP301 with 3 U of SalI (Takara Shuzo) and 3 U of HindIII (Takara Shuzo), followed by electrophoretic isolation. Separately, a 3.4 kb DNA fragment was prepared by digesting 1 μg of the pGG2 DNA with 1 U of SalI (Takara Shuzo) and 1 U of HindIII, followed by electrophoretic isolation. This 3.4 kb DNA fragment and the 140 bp DNA fragment were ligated together using 5 U of T4 DNA ligase (Takara Shuzo) and the thus-obtained plasmid was named pGG3.

DNA containing the HBsAg gene 7 was prepared by completely digesting 4 μg of pPreS (FIG. 7(A)) with 1 U of XhoI (Takara Shuzo) and 1 U of SalI (Takara Shuzo) and isolating the 1.3 kb DNA fragment 6. The DNA fragment obtained by completely digesting 1 μg of the pGG3 DNA with SalI (Takara Shuzo) was ligated with the HBsAg gene-containing 1.3 kb fragment using 5 U of T4 DNA ligase (Takara Shuzo) and the plasmid obtained was named pGG4 (FIG. 7(B)).

For the expression of the HBsAg gene in yeast, it is desirable that the HBsAg gene should be present on a self-reproducing DNA. However, pGG4 cannot reproduce itself in yeast. Therefore, 5 μg of the *Escherichia coli*-yeast shuttle vector pJDB219 DNA (Beggs, J. D., *Nature*, 275:104 (1978)) was completely digested with HindIII. A 3.2 kb DNA fragment was thus prepared. The *Escherichia coli* plasmid pBR322 DNA (1 μg) was completely digested with HindIII and ligated with the above 3.2 kb DNA fragment using 5 U of T4 DNA ligase. Thus was constructed the shuttle vector pGL5 having two HindIII sites. One of the two HindIII sites of pGL5 was rendered blunt-ended using DNA polymerase (Takara Shuzo), whereby the plasmid pGL6 having only one HindIII site (FIG. 8) was obtained.

pGL5 has the yeast 2 μ DNA-derived replication origin and the LEU2 gene (yeast-derived marker gene) on the 3.2 kb HindIII DNA fragment and, on the other fragment, it has the replication origin of *Escherichia coli* and the ampicillin resistance gene (Apc), which is a marker gene for *Escherichia coli*. To obtain the yeast replication origin and the LEU2 gene, 2 μg of the pGL5 DNA was completely digested with 1 U of HindIII and then the 3.2 kb DNA was isolated by electrophoresis. Then, pGG4 DNA (1 μg) was completely digested with 1 U of HindIII and ligated with the 3.2 kb DNA fragment using 5 U of T4 DNA ligase. The plasmid pGG5 was thus constructed (FIG. 7(B)). In this way, the vector pGG5 (FIG. 7(B)) for the production of HBsAg in yeast, which contains the promoter region having a sufficient length (652 bp) for its functioning as the GAP-DH promoter, and the HBaAg gene and the GAP-DH terminator is constructed.

REFERENCE EXAMPLE 6

Miniaturization of the GAP-DH promoter region

Figure 9:
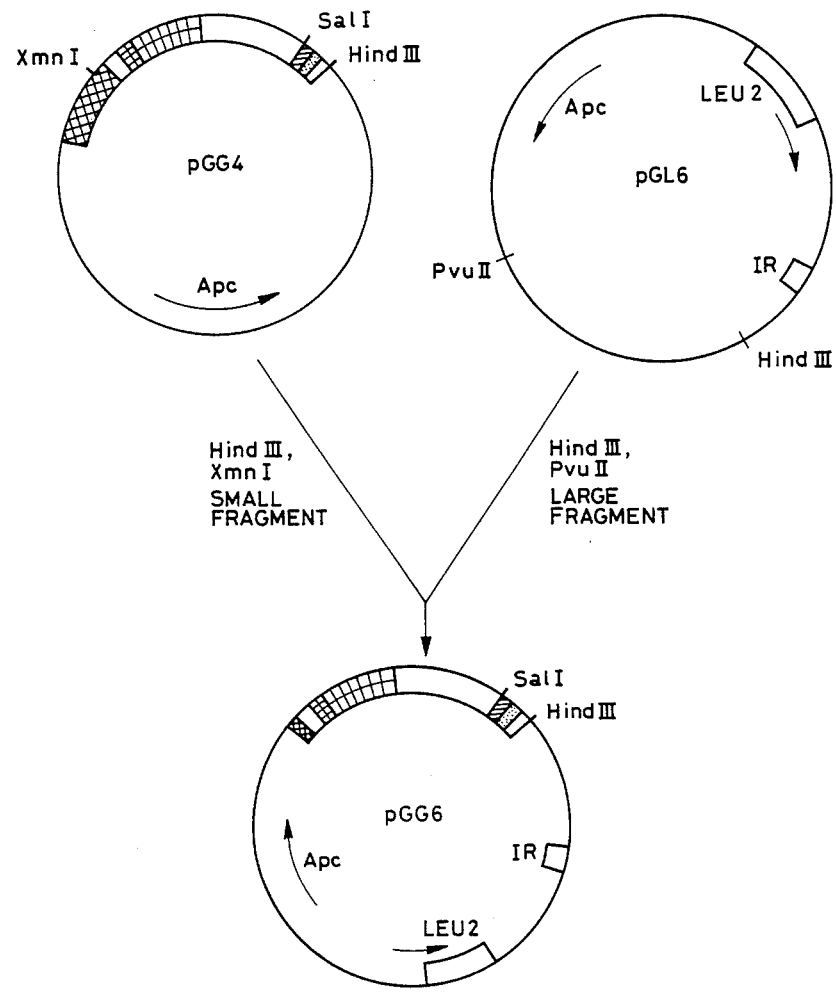
FIG. 9 shows a scheme for preparing the HBsAg production plasmid pGG6 which carries the miniaturized GAP-DH promoter.

Since the site of the promoter region for the GAP-DH gene is unknown, promoter region miniaturization was attempted using various restriction enzymes. A 1.8 kb DNA fragment containing the GAP-DH promoter (−165 bp to −25 bp), HBsAg gene and GAP terminator was prepared by completely digesting 2 μg of pGG4 with 1 U of the restriction enzyme XmnI (NEB) and 1 U of HindIII (Takara Shuzo), followed by electophoretic isolation. Separately, a 5.6 kb DNA fragment was prepared by completely digesting 1 μg of pGL6 with 1 U of PvuII (Takara Shuzo) and 1 U of HindIII (Takara Shuzo). The 1.8 kb DNA fragment and the 5.6 kb DNA fragment were ligated together using T4 DNA ligase (Takara Shuzo) and the thus-constructed plasmid containing the GAP-DH promoter shown in FIG. 3 which was named pGG6 was obtained (FIG. 9).

The yeast *Saccharomyces cerevisiae* GRF18 (a, his, leu, trp, met) strain was transormed using either pGG6 or pGG5. The transformant obtained was cultured on a leucine-free minimal medium plate comprising 0.7% (w/v) Yeast Nitrogen Base (Difco), 2% (w/v) dextrose, 1.5% (w/v) agar. The purified *Saccharomyces cerevisiae* strain GRF18/pGG6 or GRF18/pGG5 was shake-cultured on the above minimal medium (but free of agar) at 30° C. for 2 days. The culture was used as a pre-culture and inoculated into 80 ml of the same minimal medium to a concentration of 1% (w/v). After cultivation at 30° C. for 2 days, cells were harvested by centrifugation and washed once with physiological saline. A 1-mg portion of the cells was added to 16 ml of a buffer solution comprising 50 mM Tris-HCl, pH 7.5, 1.0 mM EDTA, and caused to be suspended therein. The buffer suspension was sonicated at level 10 on a Tomy Seiko model UR-200p sonicator for 9 minutes with ice cooling and then centrifuged at 0° C. and 13,000 x g for 10 minutes. The supernatant thus obtained was assayed for HBsAg activity by RPHA using Antihebcel ® (Green Cross Corp.). The results are shown in Table 2 below.

TABLE 2

| Plasmid | Host | HBsAg activity ($2^n$)* |
|---|---|---|
| pGG5 | *Saccharomyces cerevisiae* GRF18 | 12 |
| pGG6 | Same as above | 12 |

*n indicates the number of dilutions.

From the results shown in Table 2, it can be seen that the HBsAg produced by the yeast transfomred with a plasmid containing the full length GAP-DH promoter sequence (pGG5) and that of Pre S-HBsAg produced by the yeast transformed with a plasmid containing a miniaturized upstream-deleted GAP-DH promoter sequence (pGG6) are euqivalent.

REFERENCE EXAMPLE 7

Construction of Pre S-HBsAg expression vector pGG53

Figure 10:
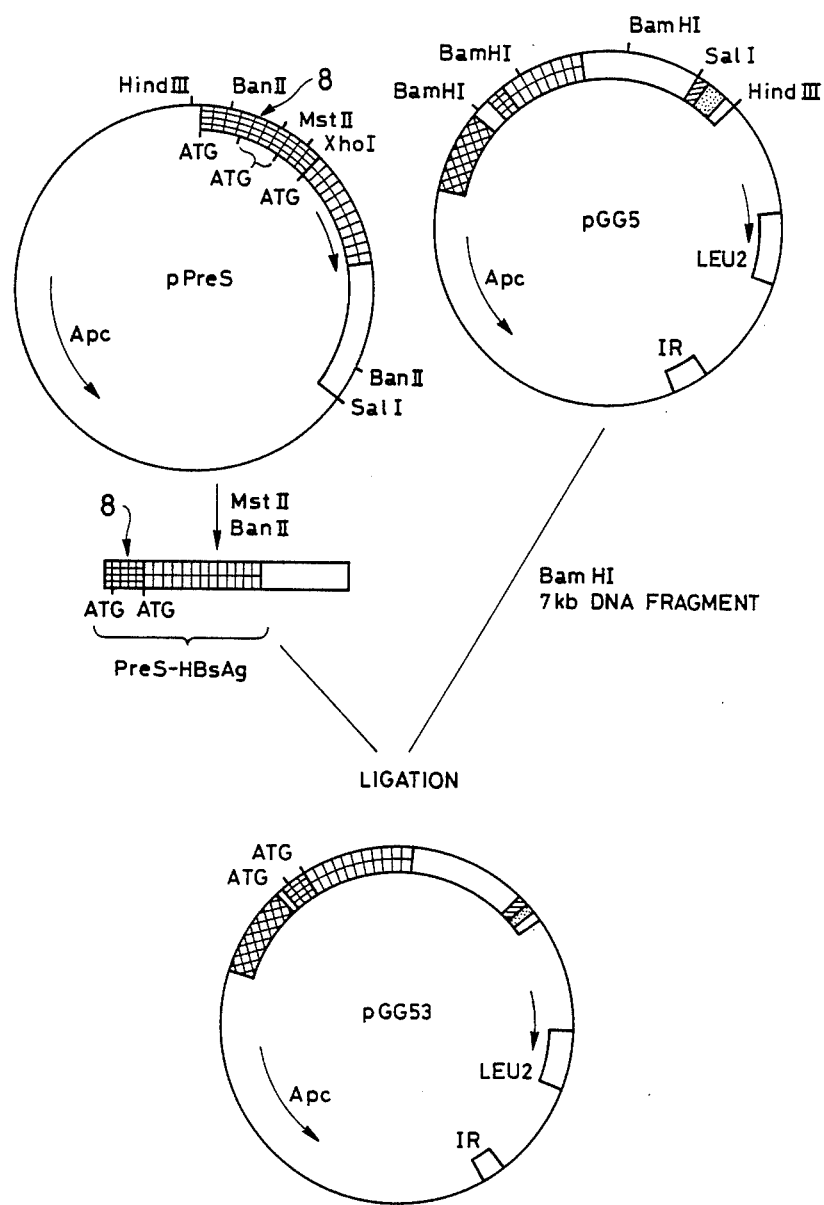
FIG. 10 shows a scheme for preparing the 3rd Pre S-HBsAg production plasmid pGG53 which carries the GAP-DH promoter.

A vector was obtained by completely digesting pGG5 (1 g) with 2 U of Bam HI (Takara Shuzo) and isolating a 7 kb DNA fragment by electrophoresis.

pPreS (FIG. 10) in an amount of 2 µg was completely digested with 2 U of MstII (NEB) and 2 U of BanII (NEB) and a 1.4 kb DNA fragment was prepared by electrophoresis. This DNA fragment codes for 3rd Pre S-HBsAg composed of HBsAg and a polyalbumin receptor-containing 55-amino-acid residue polypeptide joined thereto on the N terminus side thereof. These two DNA fragments were respectively treated with 2 U of DNA polymerase (Takara Shuzo) and dNTP (deoxyNTP) to thereby render the cohesive ends blunt. These DNA fragments were then ligated together using 5 U of T4 DNA ligase (Takara Shuzo). The resulting DNA was used to transform Escherichia coli HB101. The thus-obtained plasmid was named pGG53 (FIG. 10).

REFERENCE EXAMPLE 8

A vector was prepared by completely digesting pGG6 carrying the minaturized GAP-DH promoter and the HBsAg gene with 2 U of BamHI (Takara Shuzo) and isolating a 6 kb DNA fragment by electrophoresis.

Separately, a 1.4 kb DNA fragment was prepared by completely digesting 2 µg of pPreS carrying the Pre S gene 8 and the HBsAg gene with 2 U of MstII (NEB) and 2 U of BanII (NEB), followed by electrophoresis. This DNA fragment codes for 3rd PreS-HBsAg.

Figure 11:
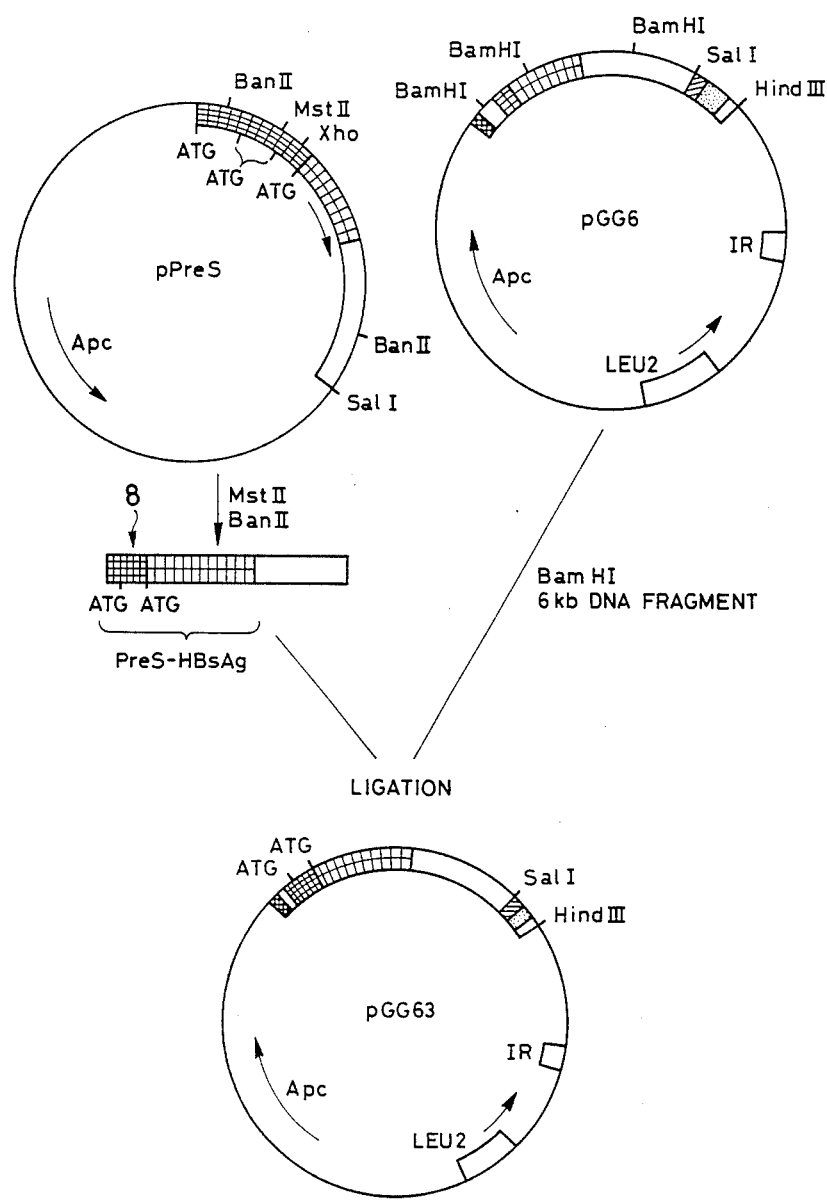
FIG. 11 shows a scheme for preparing the 3rd Pre S-HBsAg production plasmid pGG63 which carries the miniaturized GAP-DH promoter.

The above two DNA fragments were respectively treated with 2 U of DNA polymerase (Takara Shuzo) and dNTP (deoxyNTP) to thereby render the cohesive ends blunt. These DNA fragments were ligated together using 5 U of T4 DNA ligase (Takara Shuzo). The plasmid obtained as a result of transformation of Escherichia coli HB101 with the resultant DNA was named pGG63 (FIG. 11).

Then, yeast Saccharomyces cerevisiae AH22 (a, his4, leu2, can1) was transformed with pGG63 or pGG53 and each transformant obtained was cultured on a minimal medium plate comprising 0.7% (w/v) Yeast Nitrogen Base (Difco), 2% (w/v) dextrose, 1.5%(w/v) agar. The thus-purified transformants Saccharomyces cerevisiae AH22/pGG63 and Saccharomyces cerevisiae HA22/pGG53 were each shake-cultured on the above minimal medium (but free of agar) at 30° C. for 2 days. The culture was used as a preculture and inoculated into 80 ml of the same minimal medium to a concentration of 1% (w/v). After cultivation at 30° C. for 2 days, cells were collected by centrifugation and washed once with physiological saline. A 1-mg portion of the cells was added to 16 ml of a buffer comprising 50 mM Tris-HCl, pH 7.5, 1.0 mM EDTA, 1.0 mM PMSF, and caused to be suspended therein. The buffer suspension was treated on a Tomy Seiko model UR-200p sonicator at level 10 for 9 minutes with ice cooling and then subjected to centrifugation at 0° C. and 13,000 x g for 10 minutes. The supernatant was asayed for HBsAg activity using Antihebcel® (green Cross Corp.) and for polyalbumin receptor activity using an RPHA reagent obtained by sensitization of ovine erythrocytes with polyalbumin (Table 3).

Polyalbumin-sensitized erythrocytes were prepared as follows. 100 mg of human serum albumin (Miles Scientific) was dissolved in 9 ml of 0.1M phosphate buffer (ph 6.8), and 1 ml of 2.5% aqueous glutaraldehyde solution was added to the solution to prepare a mixture.

The mixture was placed in a test tube and stirred gently at 20° C. and at a rotation speed of 60 rpm for 3 hours using a slant rotar (Daiichi Radioisotope).

The mixture was transferred into a dialysis tube and dialyzed for 3 hours with exchanging 0.01M phosphate buffer saline (PBS) at pH 7.2 frequently to remove excessive glutaraldehyde.

The glutaraldehyde-treated polyalbumin in the dialysis tube was introduced in Sephadex G-200 column (1.5 cm×85 cm) equilibrated with 0.2M Tris-HCl buffered 0.2M saline (pH 8.0)(TBS) and fractionated to obtain 5 ml fractions.

Optical density at 280 nm of each fraction was measured and the fraction corresponding to the first peak was introduced in a dialysis tube and dialyzed against PBS sufficiently to prepare polyalbumin.

4 ml of 10% suspension of ovine erythrocytes and 4 ml of polyalbumin (30 mg/ml) were mixed and 2 ml of 2.5% glutaraldehyde was portionwise added to the mixture, which was then allowed to stand at room temperature for 2 hours with gentle stirring. After washing with PBS three times the product was suspended in PBS containing 1% rabbit serum and 1% sucrose (Nakarai Kagaku). The resulting suspension was used as polyalbumin-sensitized erythrocyte.

The results are shown in Table 3 below.

TABLE 3

| Plasmid | Host | HBsAG Activity (2n)* | Polyalbumin Receptor Activity (2n)* |
|---------|------|---------------------|-------------------------------------|
| pGG63 | Saccharomyces cerevisiae AH22 | 11 | 10 |
| pGG63 | Same as above | 11 | 10 |

*n indicates the number of dilutions.

From the results shown in Table 3, it can be seen that the HBsAg activity and polyalbumin receptor activity of PreS-HBsAg produced by the yeast transformed with a plasmid containing the full length GAP-DH promoter sequence (pGG53) are equivalent to the activities of Pre S-HBsAg produced by the yeast transformed with a plasmid containing a minaturized upstream-deleted GAP-DH promoter (pGG63). From this it follows that the miniaturized GAP-DH promoter exhibits a promoter activity as the full length GAP-DH promoter in the expression of Pre S-HBsAg consisting of the late part of the Pre S region beginning with the third ATG site.

The supernatant from yeast transformed with pGG63 was purified by centrifugation on a cesium chloride density gradient. The molecular weight of the purified sample was determined by SDS PAGE was about 30,000 ±2,000. The production of Pre S-HBsAg in the yeast transformant carrying pGG63 was thus confirmed. It was also confirmed that the HBsAg particles obtained had a particle size of about 22 nm as determined by electron microscopy.

REFERENCE EXAMPLE 9

Figure 12:
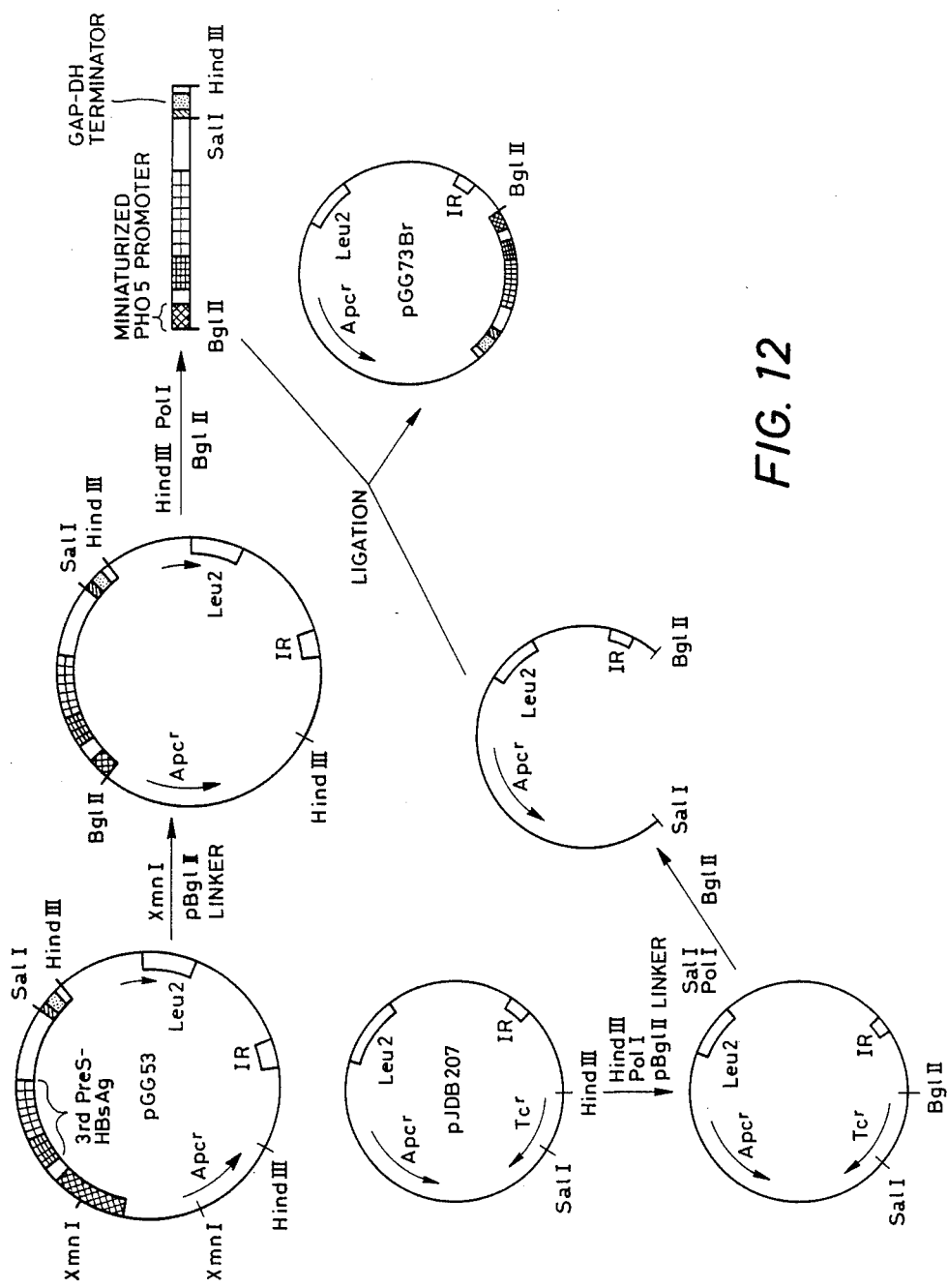
FIG. 12 shows a scheme for preparing the 3rd Pre S-HBsAg production plasmid pGG73Br which carries the miniaturized GAP-DH promoter.

Preparation of pGG73Br (FIG. 12)

pGG53 was completely digested with the restriction enzyme XmnI (NEB), and a pBlII linker (Takara Shuzo) was ligated thereto with T4 DNA ligase. The product was completely digested with HindIII. The resulting DNA fragment was blunt-ended with DNA polymerase I (Klenow fragment) followed by complete digestion with the restriction enzyme BglII (Takara Shuzo). As a result of the electrophoresis of the product using 1% agarose gel a 1.95 kb DNA fragment was obtained which contains a miniaturized GAP-DH promoter from which the region upstream from the XmmI recognition site had been removed and which contained a BglII attachment site at the 5' side end of the GAP-DH promoter, the 3rd Pre S-HBsAg gene and the GAP-DH terminator.

Separately, pJDB207 was completely digested with HindIII and the resulting DNA was blunt-ended with DNA polymerase I (Klenow fragment) followed by ligation of a BglII linker using T4 DNA ligase. The product was completely digested with SalI and the resulting DNA was blunt-ended with DNA polymerase I (Klenow fragment) followed by complete digestion with BglII. The resulting DNA fractions were subjected to electrophoresis using 0.8% agarose gel to obtain a 6.3 kb vector fragment. The 6.3 kb vector fragment and the above-described 1.95 kb fragment were ligated to each other using T4 DNA ligase to prepare pGG73Br.

EXAMPLE 1

Figure 13:
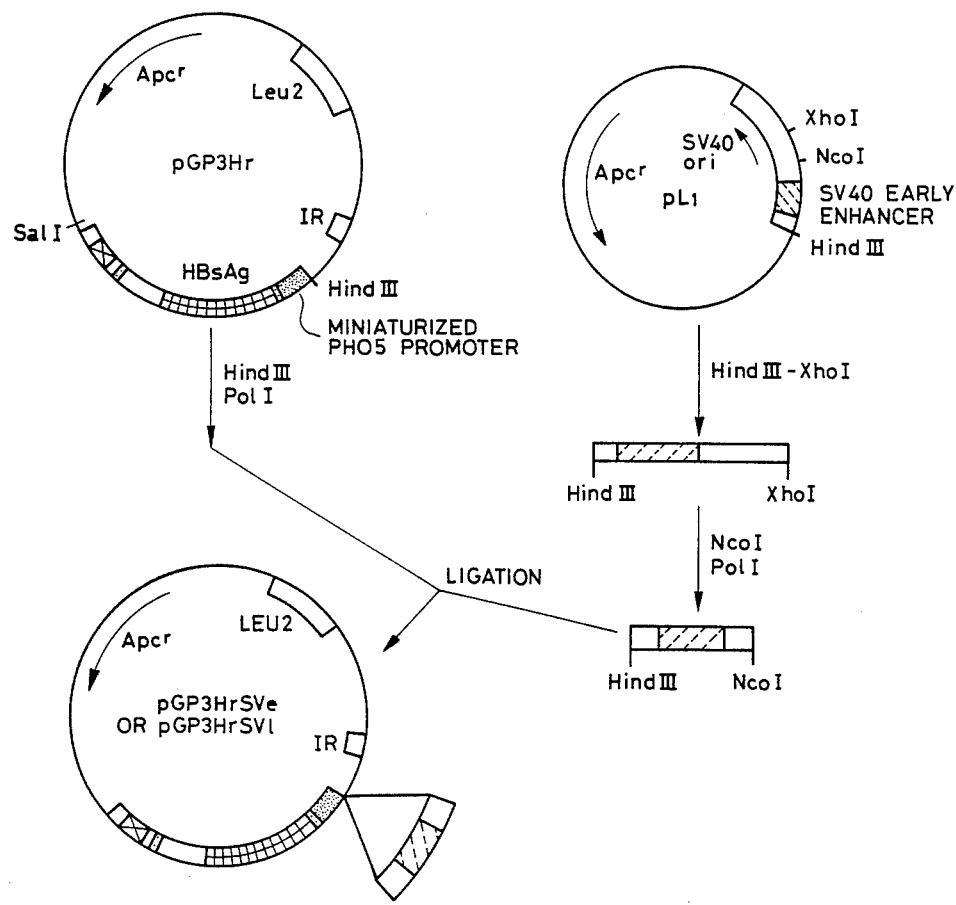
FIG. 13 shows a scheme for preparing the plasmids pGP3HrSVe and pGP3HrSVl which carry the SV40 enhancer at the early and late sides, respectively, of the reading direction of the HBsAg gene.

A 354 pb DNA fragment was prepared by completely digesting the plasmid $pL_1$ commercially available from Pharmacia AB with the restriction enzymes HindIII and XhoI (Takara Shuzo) and subjecting the digested DNA to electrophoresis using 4% polyacrylamide gel. The 354 pb DNA fragment was completelyi digested with the restriction enzyme NcoI (Boehringer-Mannheim) to obtain a 239 bp DNA fragment containing the SV early enhancer. This was blunt-ended using DNA polymerase I (Klenow fragment).

pGP3Hr obtained in REFERENCE EXAMPLE 3 after complete digestion with HindIII was blunt-ended using DNA polymerase I (Klenow fragment). The product and the 239 bp DNA fragment containing the SV40 early enhancer were ligated to each other using T4 DNA ligase. As a result, plasmids pGP3HrSVe and pGP3HrSV which, carry the SV40 enhancer at the early and late sides, respectively, of the reading direction of the HBsAg gene were obtained (FIG. 13).

Then, yeast *Saccharomyces cerevisiae* AH22 (a, his4, leu2, trp, met, pho80) strain was transformed using pGU2062. The transformant obtained was cultured on a leucine-free minimal medium plate comprising 0.7% (w/v) Yeast Nitrogen Base (Difco), 2% (w/v) dextrose and 1.5% (w/v) agar. The purified *Saccharomyces cerevisiae* strain was shake-cultured on the above minimal medium (but free of agar) at 30° C. for 2 days. The culture was used as a preculture and inoculated into 80 ml of the same minimal medium to a concentration of 1% (w/v). After cultivation at 30° C. for 2 days, cells were harvested by centrifugation and washed once with physiological saline. A 1-mg portion of the cells was added to 16 , ml of a buffer solution comprising 50 mM Tris-HCl, pH 7.5 , 1.0 mM EDTA and 1.0 mM PMSF, and caused to be suspended therein. The buffer suspension was sonicated at level 10 on a Tomy Seiko model UR-200p sonicator for 9 minutes with ice cooling and then centrifuged at 0° C. and 13,000 x g for 10 minutes. The supernatant thus obtained was assayed for HBsAg activity by RPHA using Antihebcel ® (Green Cross Corp.). The results are shown in Table 4 below.

TABLE 4

| Plasmid | Host | HBsAg Activity $(2^n)$* |
|---|---|---|
| pGL2062 | *Saccharomyces cerevisiae* GRF18pho80 | 10 |
| pGL2062 | *Saccharomyces cerevisiae* AH22 | 1 |
| pGP3Hr | *Saccharomyces cerevisiae* AH22 | 3 |
| pGP3HRSVe | *Saccharomyces cerevisiae* AH22 | >10 |
| pGP3HrSVl | *Saccharomyces cerevisiae* AH22 | >10 |

*n indicates the number of dilutions.

EXAMPLE 2

Figure 14:
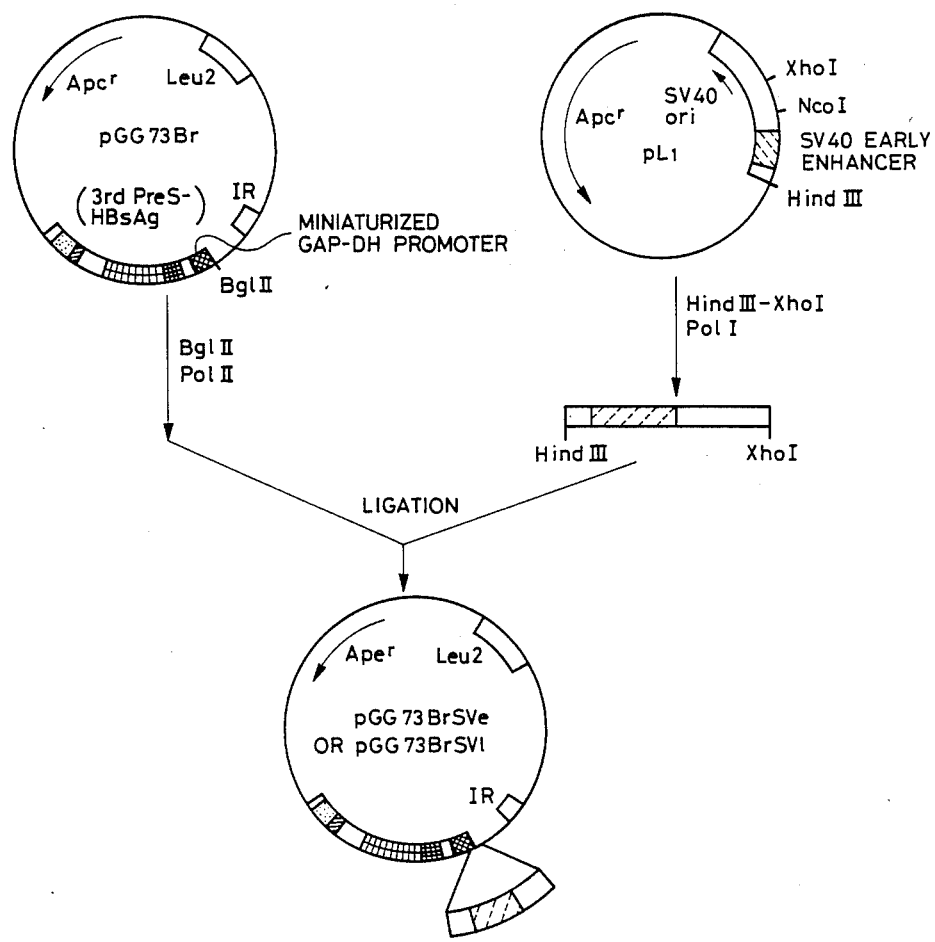
FIG. 14 shows a scheme for preparing the plasmids pGG73BrSVe and pGG73BrSVl which carry the SV40 enhancer at the early and late sides, respectively, of the reading direction of the 3rd Pre S-HBsAg gene.

In the same manner as in EXAMPLE 1, a 354 pb DNA fragment containing the SV40 early enhancer was obtained by complete digestion of $pL_1$ with HindIII and XhoI followed by electrophoresis using 4% polyacrylamide gel. This was blunt-ended using DNA polymerase I (Klenow fragment).

pGG73Br after complete digestion with BglII was blunt-ended using DNA polymerase I (Klenow fragment). The product and the 354 bp DNA fragment containing the SV40 early enhancer were ligated to each other using T4 DNA ligase. As a result, plasmids pGG73BrSVe and pGG73BrSVl which carry the SV40 enhancer at the early and late sides, respectively of the reading direction of the 3rd Pre S-HBsAg gene were obtained (FIG. 14).

Then, yeast *Saccharomyces cerevisiae* AH22 (a, his4, leu2, can1) was transformed with pGG53, pGG73Br, pGG73BrSVe or pGG73BrSVl. The transformant obtained was cultured on a leucine-free minimal medium plate comprising 0.7% (w-v) Yest Nitrogen Base (Difco), 2% (w/v) dextrose and 1.5% (w/v) agar. The purified *Saccharomyces cerevisiae* strain was shake-cultured on the above minimal medium (but free of agar) at 30° C. for 2 days. The culture was used as a preculture and inoculated into 80 ml of the same minimal medium to a concentration of 1% (w/v). After cultivation at 30° C. for 2 days, cells were harvested by centrifugation and washed once with physiological saline. A 1-mg portion of the cells was added to 16 ml of a buffer solution comprising 50 mM Tris-HCl, pH 7.5, 1.0 mM EDTA and 1.0 mM PMSF, and caused to be suspended therein. The buffer suspension was sonicated at level 10 on a Tomy Seiko model UR-200p sonicator for 9 minutes with ice cooling and then centrifuged at 0° C. and 13,000 x g for 10 minutes. The supernatant thus obtained was assayed for HBsAg activity by RPHA using Antihebcel ® (Green Cross Corp.) and for polyalbumin receptor activity using an RPHA reagent obtained by sensitization of ovine erthyrocytes with polyalbumin. The results are shown in Table 5 below.

TABLE 5

| Plasmid | Host | HBsAg Activity (2$^n$)* | Polyalbumin Receptor Activity |
|---|---|---|---|
| pGG53 | Saccharomyces cerevisiae AH22 | 7 | 6 |
| pGG73Br | Saccharomyces cerevisiae AH22 | 3 | 2 |
| pGG73BrSVe | Saccharomyces cerevisiae AH22 | 9 | 8 |
| pGG73BrSVl | Saccharomyces cerevisiae AH22 | 9 | 8 |

*n indicates the number of dilutions.

EXAMPLE 2

Preparation of 1st Pre S-HBsAg production vector

DNA fragment containing 1st Pre S-HBsAg gene was obtained by completely digesting pPre S SNA (4 μg) with 4 U of EcoRI (Takara Shuzo) and 4 U of EcoRV (Takara Shuzo) followed by elecrophoresis to obtain 1.5 kb DNA fragment.

Separately, a 6 kb DNA fragment was prepared by completely digesting pGG6 DNA (2 μg) with 2 U of BamHI (Takara Shuzo) followed by electrophoresis.

Figure 15:
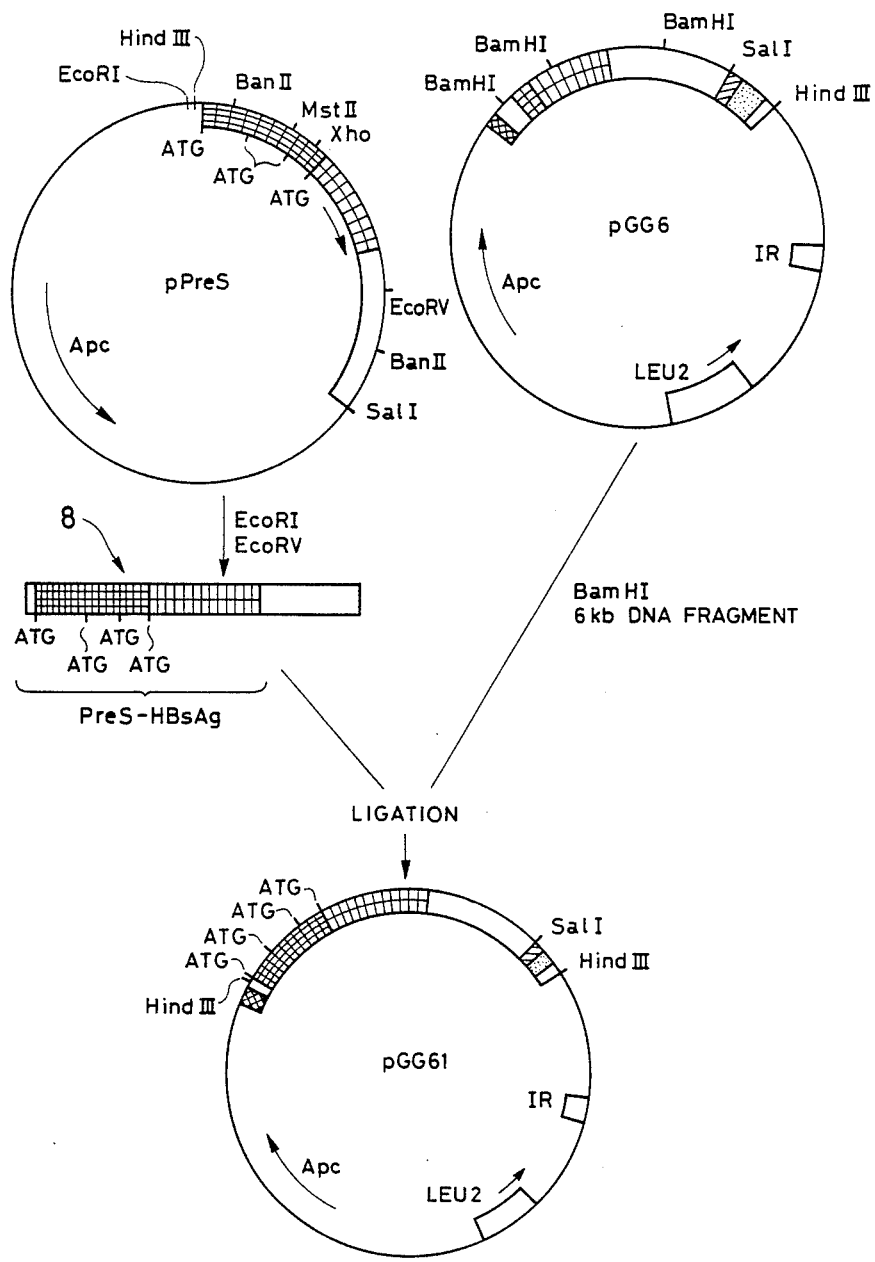
FIG. 15 shows a scheme for preparing the plasmid pGG61 which carries the 1st Pre S-HBsAg gene.
Figure 16:
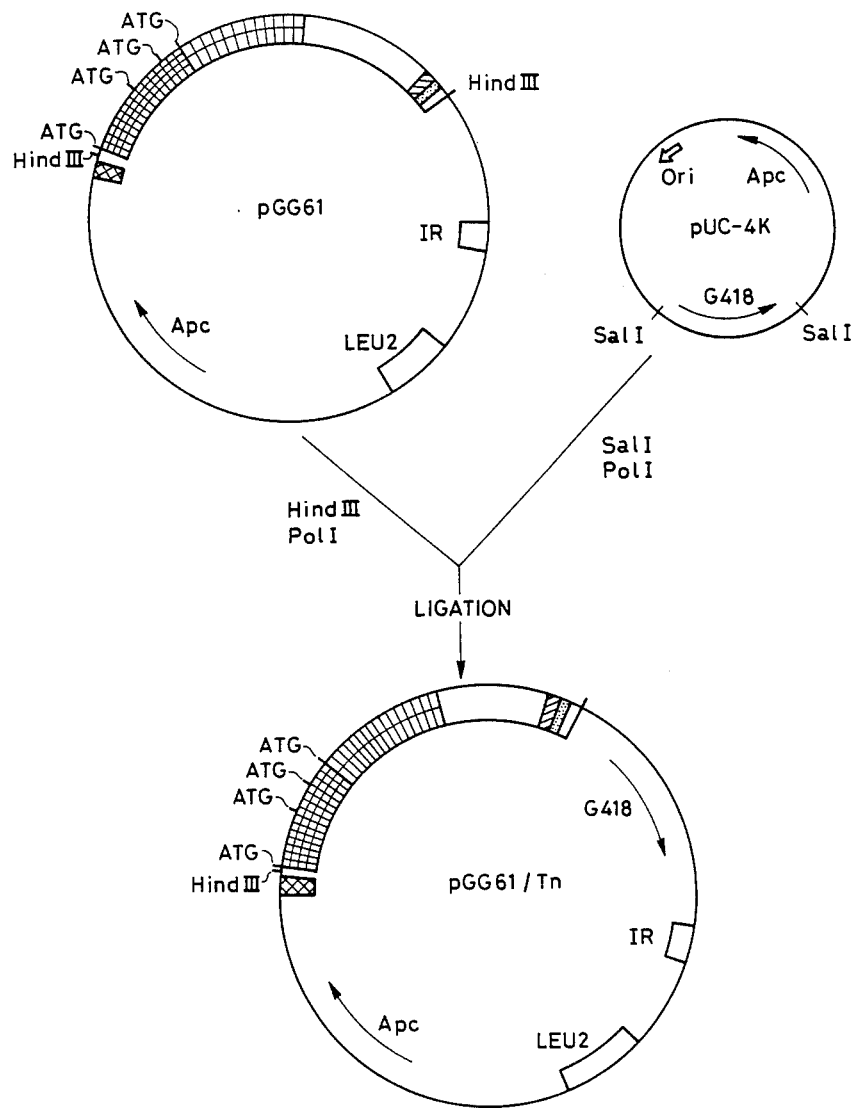
FIG. 16 shows a scheme for preparing the plasmid pGG61/Tn which carries the 1st Pre S-HBsAg gene and the G418 resistant gene.

The above two DNA fragments were each treated with DNA polymerase (Takara Shuzo) to render the cohesive ends blunt. These DNA fragments were ligated together using T4 DNA ligae (Takara Shuzo). The resultant plasmid was named pGG61 (FIG. 15).

A 5 μg portion of pGG61 DNA was partially digested with 0.1 U of HindIII to prepare a 8.0 kb DNA fragment having only one HindIII site.

Cloning vector pUC-4K DNA (5 μg) available from Pharmacia AB was completely digested with SalI (Takara Shuzo) to prepare a 1.7 kb DNA fragment containing G418 resistance gene.

Figure 17:
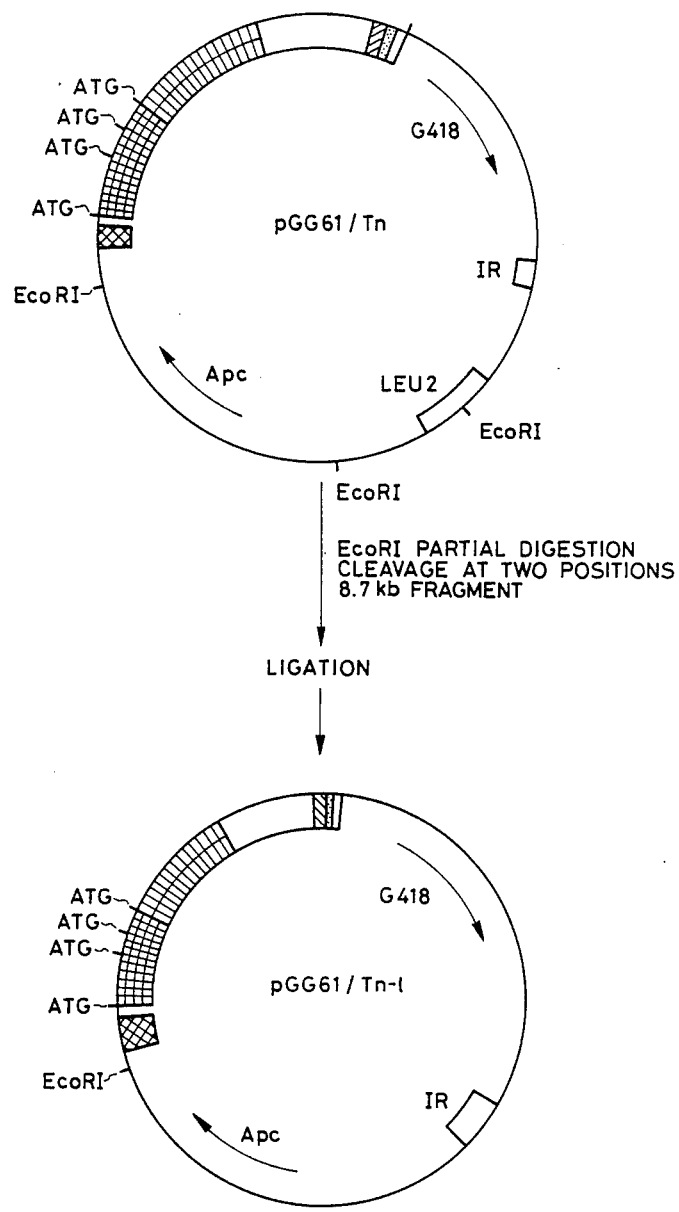
FIG. 17 shows a scheme for preparing the plasmid pGG61/Tn-l which is small-sized pGG61/Tn carrying the 1st Pre S-HBsAg gene and the G418 resistant gene.

These DNA fragments were each treated with DNA polymerase (Takara Shuzo) to render the cohesive ends blunt. The DNA fragments were ligated together using T4 DNA ligase to prepare a plasmid, which was named pGG61/Tn-l (FIG. 17).

EXAMPLE 3

Production of 1st Pre S-HBsAg in yeast

Then, the yeast Saccharomyces cerevisiae AH22 (a, his4, leu2, can1) was transformed with pGG6 and pGG/61/Tn-l to obtain transformed yeast cells which contain two kinds of plasmids, i.e., pGG6 and pGG61/Tn-l in a single cell. More particularly, transformants were obtained by adding pGG6 DNA and pGG6/Tn-l DNA to protoplasts of the yeast, diluting the resulting mixture with YNB agar medium for protoplast regeneration comprising 0.7% (w/v) Yeast Nitrogen Base (Difco), 2% (w/v) glucose (Nakarai Kagaku), 3% (w/v) agar (Difco) and 1.2M sorbitol (Nakarai Kagaku), culturing the yeast overnight at 30° C., then adding G418 (Difco) to the medium in a concentration of 40 μg/ml and culturing the yeast at 30° C. for 2 days.

Colonies formed were transplanted to 4 ml of YNB medium (supra) and cultured thereon for 2 days. Thereafter, the transformant was transplanted on YPD medium (supra) further containing 250 μg/ml G418 (Difco) for 1 day.

Cells were harvested by centrifugation, washed once comprising 50 mM Tris-HCl, pH 7.5, 1.0 mM EDTA, 1.0 mM PMSF. The suspension was treated on a Tomy Seiko model UR-200p sonicator at level 10 for 9 minutes with ice cooling and then subjected to centrifugation at 0° C. and 13,000 x g for 10 minutes. The supernatant thus obtained was assayed for HGsAg activity using Antihebcel ® (Green Cross Corp.) and for polyalbumin receptor activity using an RPHA reagent obtained by sensitization of ovine erythrocytes with polyalbumin. The results are shown in Table 6 below.

TABLE 6

| Plasmid | Host | HBsAg Activity (2$^n$)* | Polyalbumin Receptor Activity (2$^n$)* |
|---|---|---|---|
| pGG6 + pGG61/Tn-l | Saccharomyces cerevisiae AH22 | 11 | 6 |
| pGG63 | Same as above | 12 | 12 |

*n indicates the number of dilutions.

From the results shown in Table 6, it can be seen that the HBsAg activity and polyalbumin receptor activity of Pre S-HBsAg produced by the yeast co-transformed with a plasmid containing full length (1st) Pre S (pGG61/Tn-l) and a plasmid containing small-sized (3rd) Pre S sequence (pGG6) are not less potent than the activities of Pre S-HBsAg produced by the yeast transformed singly with a plasmid containing small-sized (2nd) Pre S sequence (pGG63).

Further, the HBsAg activity and polyalbumin receptor activity of the above Pre S-HBsAg were determined by the EIA method. Auszyme (Abbott) was used for the detemination of the HBsAg activity and for the polyalbumin activity HB$_{AR}$ test (Institute of Medical Biological Research) was employed. The determination was carried out according to the methods recommended.

The results obtained are shown in Table 7 below.

TABLE 7

| Plasmid | HBsAg Activity (mg/l) | Polyalbumin Receptor Activity (U/l) |
|---|---|---|
| pGG6 + pGG61/Tn-l | 0.36 | 110 |
| pGG63 | 0.69 | 520 |

Human albumin (Miles Scientific) was polymerized with glutaraldehyde (Nakarai Kagaku) to prepare human polyalbumin, which was adsorbed on CNBr-activated Sepharose 4B (Pharmacia AB) to prepare a polyalbumin affinity column.

HBsAg-positive cell supernatant sample was applied to this column. After washing it sufficiently with 20 times the gel volume of washing buffer comprising 50 mM aris (Nakarai Kagaku), 5 mM PMSF (Sigma), 10 mM EDTA (Nakarai Kagaku), 0.1% (w/v) sodium azide (Nakarai Kagaku) and 0.15M NaCl (Nakarai Kagaku), the column was eluted with double the gel volume of the washing buffer further comprisifng 5M quanidine chloride (Nakarai Kagaku).

After dialysis with the eluent, the dialysate was centrifuged and the resulting supernatant was concentrated using centricon 10 (Amicon).

The concentrate was subjected to electrophoresis using 10% SDS-polyacrylamide gel. Two bands corresponding to the molecular weights of about 41,000 and about 24,000 were confirmed. Further, the gel was subjected to Western blotting using $^{125}$I-labelled anti-HBsAg antibody. Two bands corresponding to the molecular weights of about 41,000 and about 24,000 were confirmed. It was thus confirmed that the transformed cells had produced Pre S-HBsAg peptides.

While the invention has been described in detail and with reference to specific embodiments thereof, it will be apparent to one skilled in the art that various changes and modifications can be made therein without departing from the spirit and scope thereof.

What is claimed is:

1. A method of producing a heterologous protein in yeast which comprises transforming a yeast *Saccharomyces cerevisiae* with recombinant DNA comprising a hybrid promoter consisting essentially of *Saccharomyces cerevisiae* PHO5 or GAP-DH promoter from which the upstream activation site (UAS) has been deleted and replaced with the early enhancer region derived from SV40 virus and a gene coding for the heterologous protein, culturing the resulting transformed cells under conditions that permit expression of the gene coding for the heterologous protein, and isolating the heterologous protein from the culture medium.

2. The method as claimed in claim 1, wherein said glyceraldehyde-3 phosphate dehydrogenase (GAP-DH) promter or repressible acid phosphatase PHO5) promoter from which the UAS has been delated has a nucleotide sequence substantially corresponding to that shown in FIG. 3 and FIG. 2, respectively.

3. The method as claimed in claim 1, wherein said heterologous protein is HBsAg or Pre S-HBsAg.

4. The method as claimed in claim 3, wherein said heterologous protein in Pre S-HBsAg in which the Pre S region comprises at least the 55 amino acid sequence

| "Met | His | Trp | Asn | Ser | Thr | Thr | Phe | His | Gln 10 |
|---|---|---|---|---|---|---|---|---|---|
| Thr | Leu | Gln | Asp | Pro | Arg | Val | Arg | Gly | Leu 20 30 |
| Tyr | Phe | Pro | Ala | Gly | Gly | Ser | Ser | Ser | Gly 40 |
| Thr | Val | Asn | Pro | Val | Pro | Thr | Thr | Thr | Ser 50 |
| Pro | Ile | Ser | Ser | Ile 55 | Phe | Ser | Arg | Ile | Gly |

-continued

| Asp | Pro | Ala | Leu | Asn." |
|---|---|---|---|---|

5. The method as claimed in claim 1, wherein said heterologous protein is full length Pre S-HBsAg.

6. The method as claimed in claim 5, "wherein the promotor from which the UAS has been deleted is the GAP-DH promotor."

7. The method as claimed in claim 5, "wherein the promotor from which the UAS has been deleted is the GAP-DH promotor which comprises a DNA sequence from at least the −25th base pair to the −164th base pair upstream from the initiation codon."

8. The method as claimed in claim 5, wherein the expression of said full length Pre S-HBsAg is carried out in the same yeast cell as that in which a DNA sequence coding for 3rd Pre S-HBsAg is expressed.

9. The method as claimed in claim 2, wherein said heterologous protein is HBsAg or Pre S-HBsAg.

10. The method as claimed in claim 9, wherein said heterologous protein is Pre S-HBsAg in which the Pre S region comprises at least the 55 amino acid sequence

| Met | His | Trp | Asn | Ser | Thr | Thr | Phe | His | Gln 10 |
|---|---|---|---|---|---|---|---|---|---|
| Thr | Leu | Gln | Asp | Pro | Arg | Val | Arg | Gly | Leu 20 30 |
| Tyr | Phe | Pro | Ala | Gly | Gly | Ser | Ser | Ser | Gly 40 |
| Thr | Val | Asn | Pro | Val | Pro | Thr | Thr | Thr | Ser 50 |
| Pro | Ile | Ser | Ser | Ile 55 | Phe | Ser | Arg | Ile | Gly |
| Asp | Pro | Ala | Leu | Asn | | | | | |

11. A hybrid promoter consisting essentially of a *Saccharomyces cerevisiae* repressible acid phosphatase (PHO5) or glyceraldehyde-3 phosphate dehydrogenase (GAP-DH) promoter from which the upstream activation site (UAS) is delated and replaced with the early enhancer region derived from SV40 virus.

12. The hybrid promoter as claimed in claim 11, wherein said GAP-DH promoter or PHO5 promoter from which the UAS has been deleted has a nucleotide sequence substantially corresponding to that shown in FIG. 3 and FIG. 2, respectively.

* * * * *